US008318424B2

(12) United States Patent
Weeks et al.

(10) Patent No.: US 8,318,424 B2
(45) Date of Patent: Nov. 27, 2012

(54) HIGH-THROUGHPUT RNA STRUCTURE ANALYSIS

(75) Inventors: Kevin M. Weeks, Carrboro, NC (US);
Stefanie A Mortimer, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 342 days.

(21) Appl. No.: 12/227,987

(22) PCT Filed: Jun. 5, 2007

(86) PCT No.: PCT/US2007/013226
§ 371 (c)(1),
(2), (4) Date: Oct. 29, 2009

(87) PCT Pub. No.: WO2007/145940
PCT Pub. Date: Dec. 21, 2007

(65) Prior Publication Data
US 2010/0035761 A1    Feb. 11, 2010

Related U.S. Application Data

(60) Provisional application No. 60/810,960, filed on Jun. 5, 2006, provisional application No. 60/854,650, filed on Oct. 26, 2006, provisional application No. 60/878,724, filed on Jan. 5, 2007.

(51) Int. Cl.
*C12Q 1/68* (2006.01)
*C07H 21/02* (2006.01)

(52) U.S. Cl. ........................................ 435/6.1; 536/23.1

(58) Field of Classification Search .......................... None
See application file for complete search history.

(56) References Cited

U.S. PATENT DOCUMENTS
6,794,140 B1 *  9/2004  Goldsborough .................. 435/6
2010/0035761 A1  2/2010  Weeks

FOREIGN PATENT DOCUMENTS
WO    WO 2007/145940     12/2007

OTHER PUBLICATIONS

Merino et al. Journal of the American Chemical Society (2005) 127: 4223-4231.*
Robins et al. Journal of Organic Chemistry (2001) 66: 8204-8210.*
Berkhout et al. (1996). Structure and Function of the Human Immunodeficiency Virus Leader RNA. Prog Nucleic Acid Res. Mol Biol. 54:1-34.
Cheong et al. (1990). Solution structure of an unusually stable RNA hairpin, 5'GGAC(UUCG)GUCC. Nature. 346:680-682.
Merino et al. (2004). View an RNA melt with single nucleotide resolution. 228th ACS National Meeting, Philadelphia, PA, Aug. 22-26, 2004.
U.S. Appl. No. 60/810,960, filed Jun. 5, 2006, Weeks.

U.S. Appl. No. 60/854,680, filed Oct. 26, 2006, Weeks.
U.S. Appl. No. 60/878,724, filed Jan. 5, 2007, Weeks.
Amarasinghe et al. (2000). NMR structure of the HIV-1 nucleocapsid protein bound to stem-loop SL2 of the psi-RNA packaging signal. Implications for genome recognition. J Mol Biol. 301:491.
Badorrek et al. (2005). RNA flexibility in the dimerization domain of a gamma retrovirus. Nature Chem Biol. 1:104-11.
Badorrek et al. (2006a). Structure of an RNA switch that enforces stringent retroviral genomic RNA dimerization. Proceedings of the National Academy of Sciences USA. 103:13640-13645.
Badorrek et al. (2006b). Architecture of a gamma retroviral genomic RNA dimer. Biochemistry, 45.12664-12672.
Barrick et al. (2004). New RNA motifs suggest an expanded scope for riboswitches in bacterial genetic control. Proceedings of the National Academy of Sciences, USA. 101:6421-6426.
Baudin, et al. (1993). Functional Sites in the 5' Region of Human Immunodeficiency Virus Type 1 RNA Form Defined Structural Domains. J Mol Biol. 229:382-397.
Berkhout et al. (2002). In Vitro Evidence That the Untranslated Leader of the HIV-1 Genome is an RNA Checkpoint That Regulates Multiple Functions through Conformational Changes. J Biol Chem. 277:19967-19975.
Berkowitz (1996). RNA packaging. Curr Top Micorbiol Immunol. 214:177.
Brenowitz (1986). Quantitative DNase footprint titration: A method for studying protein-DNA interactions. Methods Enzymol. 130:132-181.
Brion & Westhof (1997). Hierarchy and dynamics of RNA folding. Rev. Biophsy. Biomol. Struct. 26, 113-137.
Burns et al. (1993). Vesicular stomatitis virus G glycoprotein pseudotyped retroviral vectors: concentration to very high titer and efficient gene transfer into mammalian and nonmammalian cells. Proceedings of the National Academy of Sciences USA. 90:8033-8037.
Cardinaud et al. (1970). Irreversible enzyme inhibitors. CLXXII. Proteolytic enzymes. XVI. Covalent bonding of the sulfonyl fluoride group to serine outside the active-site of .alpha.-chymotrypsin by exo-type active-site directed irreversible inhibitors. J. Med. Chem. 13:467-470.
Chamberlin et al. (2000). Mapping Local Nucleotide Flexibility by Selective Acylation of 2'-Amine Substituted RNA. J Am Chem Soc. 122:216-224.
Chamberlin et al. (2002). Catalysis of amide synthesis by RNA phosphodiester and hydroxyl groups. Proceedings of the National Academy of Sciences USA. 99:14688-14693.
Chamberlin et al. (2003). Differential Helix Stabilities and Sites Pre-organized for Tertiary Interactions Revealed by Monitoring Local Nucleotide Flexibility in the bI5 Group I Intron RNA. Biochemistry. 42:901-909.
Chen et al. (2006). Structure of stem-loop IV of Tetrahymena telomerase RNA. EMBO J. 25:3156-3166.

(Continued)

*Primary Examiner* — Angela M Bertagna
(74) *Attorney, Agent, or Firm* — Jenkins, Wilson, Taylor & Hunt, P.A.

(57) ABSTRACT

The presently disclosed subject matter relates to technology and methods for analyzing the structure of RNA molecules. More particularly, the presently disclosed subject matter is directed to methods of, compositions for, and computer program products for RNA structure analysis through alkoxide-selective 2'-hydroxyl acylation analyzed by primer extension.

5 Claims, 10 Drawing Sheets

OTHER PUBLICATIONS

Chetouani et al. (1997). ESSA: an integrated and interactive computer tool for analysing RNA secondary structure. Nucleic Acids Res. 25:3514-3522.

Damgaard et al. (2004). RNA Interactions in the 5' Region of the HIV-1 Genome. J Mol Biol. 336:369-379.

Das et al. (2005). SAFA: semi-automated footprinting analysis software for high-throughput quantification of nucleic acid footprinting experiments. RNA. 11:344-354.

De Belder et al. (1975). Preparation and properties of fluorescein-labelled hyaluronate. Carbohydrate Res. 44:251-257.

De Guzman et al (1998). Structure of the HIV-1 nucleocapsid protein bound to the SL3 Ψ-RNA recognition element. Science. 279:384-388.

Doshi et al. (2004). Evaluation of the suitability of free-energy minimization using nearest-neighbor energy parameters for RNA secondary structure prediction. BMC Bioinformatics. 5:105.

Dowell et al. (2004). Evaluation of several lightweight stochastic context-free grammars for RNA secondary structure prediction. BMC Bioinformatics. 5: 71.

Eddy (2004). How do RNA folding algorithms work? Nature Biotech. 22:1457-1458.

Ehresmann et al. (1987). Probing the structure of RNAs in solution. Nucleic Acids Res. 15:9109-9128.

Frankel et al. (1998) HIV-1: fifteen proteins and an RNA. Ann Rev Biochem. 67:1-25.

Fu et al. (1994). Characterization of human immunodeficiency virus type 1 dimeric RNA from wild-type and protease-defective virions. J Virol. 68:5013-5018.

Genbank AF324493, 2010.

Gherghe et al (2006). The SL1-SL2 (stem loop) domain is the primary determinant for stability of the gamma retroviral genomic RNA dimer. J Biol Chem. 281:37952.

Gherghe et al. (2008). Strong correlation between SHAPE chemistry and the generalized NMR order parameter (S2) in RNA. J Am Chem Soc. 130(37):12244-5.

Giddings et al. (1998). A software system for data analysis in automated DNA sequencing. Genome Res. 8:644-665.

Helm, M. et al. (1998). The presence of modified nucleotides is required for cloverleaf folding of a human mitochondrial tRNA. Nucl. Acids Res. 26:1636-1643.

Hiratsuka (1983). New ribose-modified fluorescent analogs of adenine and guanine nucleotides available as substrates for various enzymes Biochem Biophys Acta. 742: 496-508.

Hogeweg et al. (1984). Energy directed folding of RNA sequences. Nucleic Acids Res. 12:67-74.

International Preliminary Report on Patentability for International Application No. PCT/US2007/13226, dated Oct. 12, 2008.

International Search Report for International Application No. PCT/US2007/13226, dated Oct. 4, 2008.

Isel (1999). Structural basis for the specificity of the initiation of HIV-1 reverse transcription. EMBO. 18:1038-1048.

John, D.M. et al. (2000a). Tagging DNA mismatches by selective 2'-amine acylation. Chem Biol. 7:405-410.

John, D.M. et al. (2000b). van't Hoff enthalpies without baselines. Protein Sci. 9:1416-1419.

John, D.M. et al. (2002). Chemical interrogation of mismatches in DNA-DNA and DNA-RNA duplexes under nonstringent conditions by selective 2'-amine acylation. Biochemistry. 41:6866-6874.

John, D.M. et al. (2004). Mechanics of DNA Flexibility Visualized by Selective 2'-Amine Acylation at Nucleotide Bulges. J. Mol. Biol. 337: 611-619.

Jones et al. (2008). Lack of secondary structure characterizes the 5' ends of mammalian mitochondrial mRNAs. RNA. (5):862-71.

Knapp, G. (1989). Enzymatic approaches to probing of RNA secondary and tertiary structure. Methods Enzymol. 180: 192-212.

Krasilnikov et al. (2003). Crystal structure of the specificity domain of ribonuclease P. Nature. 421:760-64.

Laederach et al. (2008). Semi-automated and rapid quantification of nucleic acid footprinting and structure mapping experiments. Nat Protoc. 3(9):1395-401. Author manuscript at http://safa.standford.edu.

Larson et al. (1987). The function of proteins that interact with mRNA. Mol Cell Biochem. 74:5-15.

Mathews et al. (1999). Expanded sequence dependence of thermodynamic parameters improves prediction of RNA secondary structure. J Mol Biol. 288:911-940.

Mathews et al. (2004). Incorporating chemical modification constraints into a dynamic programming algorithm for prediction of RNA secondary structure. Proceedings of the National Academy of Sciences USA. 101:7287-7292.

Mathews et al. (2006). Prediction of RNA secondary structure by free energy minimization. Curr Opin Struct Biol. 16:270-278.

Matzura et al. (1996). RNAdraw: an integrated program for RNA secondary structure calculation and analysis under 32-bit Microsoft Windows. CABIOS. 12:247-249.

Merino et al. (2005). RNA Structure Analysis at Single Nucleotide Resolution by Selective 2'-Hydroxyl Acylation and Primer Extension (SHAPE). Journal of the American Chemical Society.127:4223-4231.

Milligan et al. (1989). Synthesis of small RNAs using T7 RNA polymerase. Methods Enzymol. 180:51-62.

Moorman et al. (1982). New class of serine protease inactivators based on isatoic anhydride. J. Am Chem. 104: 6785-6786.

Mortimer & Weeks (2007). A fast-acting reagent for accurate analysis of RNA secondary and tertiary structure by SHAPE chemistry. J Am Chem Soc. 129:4144-4145.

Notice of References Cited corresponding to U.S. Appl. No. 12/227,987, dated Mar. 28, 2011.

Notice of References Cited corresponding to U.S. Appl. No. 12/227,987, dated Oct. 13, 2011.

Nussinov et al. (1978). Algorithms for loop matchings. J. Appl. Math. 35:68-82.

Office Action corresponding to U.S. Appl. No. 12/227,987, dated Oct. 13, 2011.

Office Action corresponding to U.S. Appl. No. 12/227,987 dated Mar. 28, 2011.

Osterburg et al. (1981). Comput Prog. Biomed. 13:101-109.

Paegel, B.M. (2002). High throughput DNA sequencing with a microfabricated 96-lane capillary arra electrophoresis bioprocessor. Proceedings of the National Academy of Sciences, USA. 99:574-579.

Paillart et al. (2002). In vitro evidence for a long range pseudoknot in the 5'-untranslated and matrix coding regions of HIV-1 genomic RNA. J. Biol Chem. 277:5995-6004.

Paillart et al. (2004a). First snapshots of the HIV-1 RNA structure in infected cells and in virions. J. Biol Chem. 279:48397-48403.

Paillart et al. (2004b). Dimerization of retroviral RNA genomes: an inseparable pair. Nature Rev. Microbiol. 2:461-472.

Peattie et al. (1980). Chemical probes for higher-order structure in RNA. Proceedings of the National Academy of Sciences, USA. 77: 4679-4682.

Perret (1990). Conformation in solution of yeast tRNA(Asp) transcripts deprived of modified nucleotides. Biochimie. 72:735-743.

Puglisi et al. (1992). Conformation of the TAR RNA-arginine complex by NMR spectroscopy. Science. 257:76-80.

Rein (1998). Nucleic-acid-chaperone activity of retroviral nucleocapsid proteins: significance for viral replication. Trends Biochem Sci. 23:297-301.

Rein (2004). Take Two. Nature Struct Mol Biol. 11:1034-1035.

Resnekov (1989). RNA secondary structure is an integral part of the in vitro mechanism of attenuation in simian virus 40. J. Biol Chem. 264:9953-9959.

Romby et al. (1987). Comparison of the tertiary structure of yeast tRNA(Asp) and tRNA(Phe) in solution. Chemical modification study of the bases. J. Mol Biol. 195:193-204.

Rossio et al. (1998). Inactivation of human immunodeficiency virus type 1 infectivity with preservation of conformational and functional integrity of virion surface proteins. J. Virol. 72: pp. 7992-8001.

Stearns et al. (1997). Synthesis and characterization of highly sensitive heparin probes for detection of heparin-binding proteins. Anal. Biochem. 247: 348-356.

Soukup & Breaker (1999). Relationship between internucleotide linkage geometry and the stability of RNA. RNA. 5:1308-1325.

Thomas et al. (2006). Human immunodeficiency virus type 1 nucleocapsid zinc-finger mutations cause defects in reverse transcription and integration. Virology, 353:41-51.

Tinoco et al. (1987). RNA structure from A to Z. Cold Spring Harb Symp Quant Biol. 52:135-146.

Tinoco et al. (1999). How RNA folds. J Mol Biol. 293:271-281.

Tuerk et al. (1988). CUUCGG hairpins: Extraordinarily stable RNA secondary structures associated with various biochemical processes. Proceedings of the National Academy of Sciences USA. 85:1364-1368.

Vasa et al. (2008). ShapeFinder: a software system for high-throughput quantitative analysis of nucleic acid reactivity information resolved by capillary electrophoresis. RNA. (10):1979-90.

Velikyan et al. (2001). J Am Chem Soc. 123: 2893-2894.

Verheyden et al. (1971). Synthesis of some pyrimidine 2'-amino-2'-deoxynucleosides. J Org. Chem. 36:250-254.

Wang et al (2008). Complex ligand-induced conformational changes in tRNA(Asp) revealed by single-nucleotide resolution SHAPE chemistry. Biochemistry. 47(11):3454-61.

Westhof et al. (1985). Crystallographic refinement of yeast aspartic acid transfer RNA. J Mol Biol. 184:119-145.

Westhof et al. (1988). Restrained refinement of two crystalline forms of yeast aspartic acid and phenylalanine transfer RNA crystals. Acta Crystallogr A. 44:112-123.

Wilkinson et al. (2005). RNA SHAPE chemistry reveals nonhierarchical interactions dominate equilibrium structural transitions in tRNA(Asp) transcripts. J Am Chem Soc. 127:4659-4667.

Wilkinson et al. (2006). Selective 2'-hydroxyl acylation analyzed by primer extension (SHAPE): quantitative RNA structure analysis at single nucleotide resolution. Nature Protocols. 1:1610-1616.

Wilkenson et al. (2008). High-throughput SHAPE analysis reveals structures in HIV-1 genomic RNA strongly conserved across distinct biological states. PLoS Biol. 6:e96.

Wittberger et al. (2000). Evaluation of uranyl photocleavage as a probe to monitor ion binding and flexibility in RNAs. J. Mol. Biol. 300: 339-352.

* cited by examiner

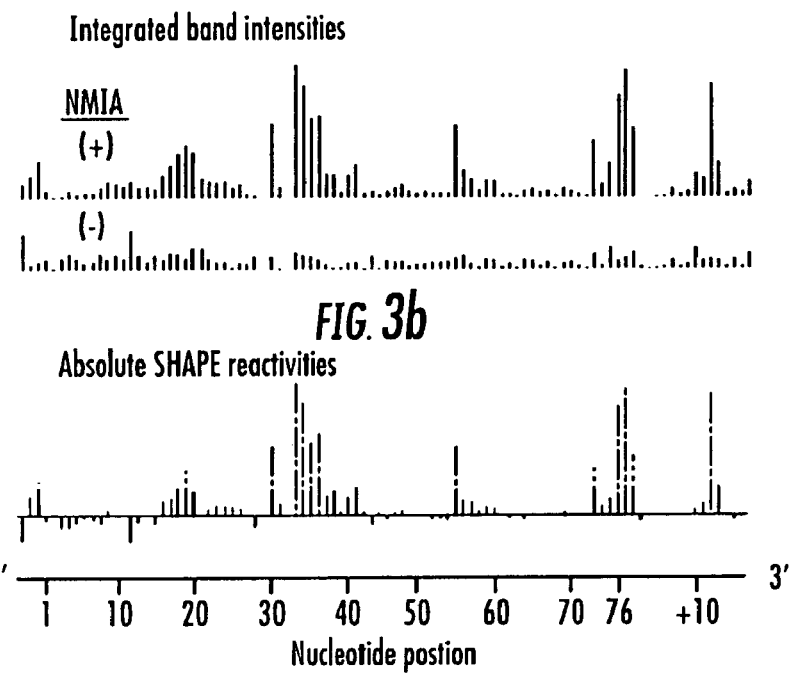
FIG. 3b
FIG. 3c
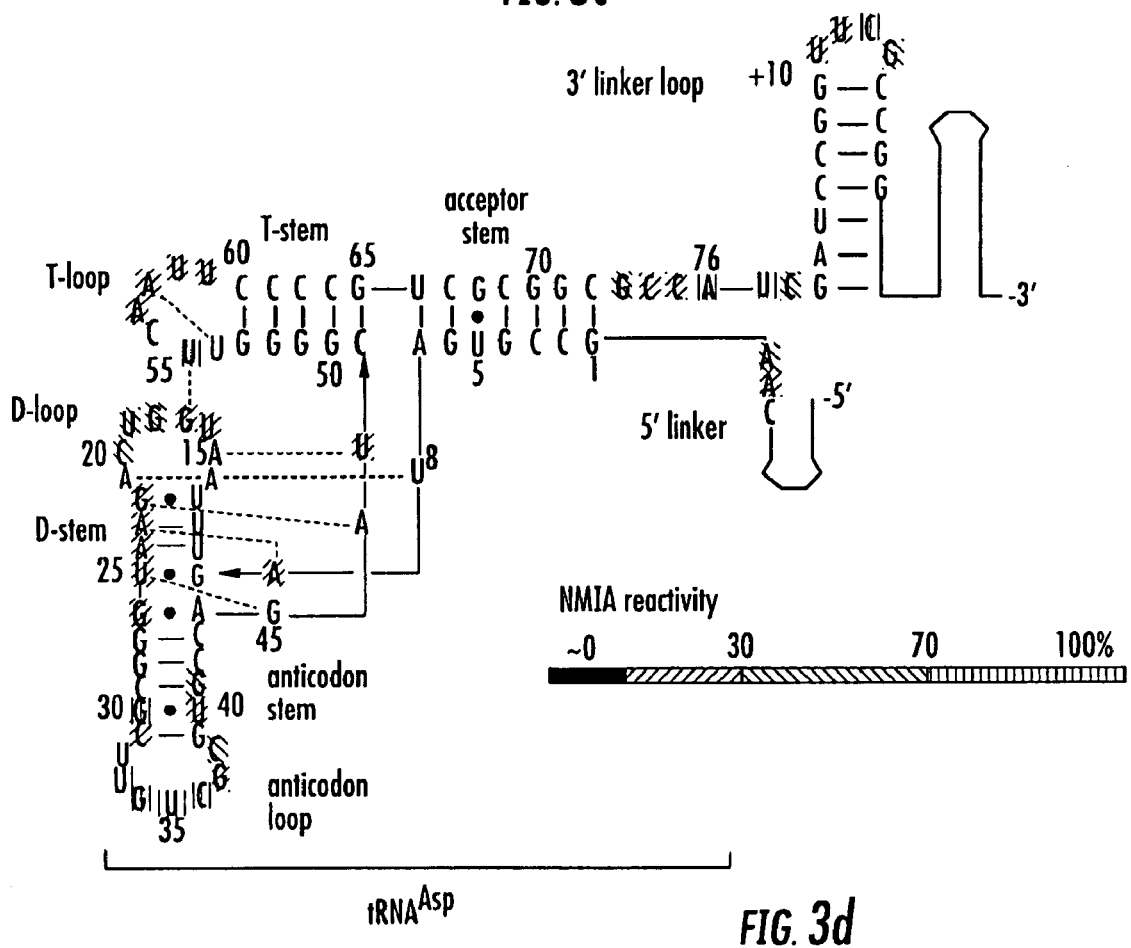
FIG. 3d

HIGH-THROUGHPUT RNA STRUCTURE ANALYSIS

RELATED APPLICATIONS

This application claims the benefit of U.S. Provisional Patent Application Ser. No. 60/810,960, filed Jun. 5, 2006; U.S. Provisional Patent Application Ser. No. 60/854,650, filed Oct. 26, 2006; and U.S. Provisional Patent Application Ser. No. 60/878,724, filed Jan. 5, 2007; the disclosures of which are incorporated herein by reference in their entireties.

GOVERNMENT INTEREST

This presently disclosed subject matter was made with U.S. Government support under Grant No. MCB-9984289 awarded by the National Science Foundation (NSF), and Grant Nos. AI068462 and GM076485 awarded by the National Institutes of Health (NIH). The presently disclosed subject matter was also supported with federal funds from the National Cancer Institute, NIH under contract NO1-CO-12400, and by the Intramural Research Program of the NIH, National Cancer Institute, and Center for Cancer research. Thus, the U.S. Government has certain rights in the presently disclosed subject matter.

TECHNICAL FIELD

The presently disclosed subject matter relates to technology and methods for analyzing the structure of RNA molecules. More particularly, in some embodiments the presently disclosed subject matter is directed to methods of RNA structure analysis through alkoxide-selective 2'-hydroxyl acylation analyzed by primer extension.

ABBREVIATIONS

1M7—1-methyl-7-nitroisatoic anhydride
3-AMBC—3-aminomethylbenzoyl chloride
3-CBC—3-carboxybenzoyl chloride
4-CBC—4-carboxybenzoyl chloride
4NPA—4-nitrophthalic anhydride
AT-2—2-aldrithiol
BC—benzoyl cyanide
BCl—benzoyl chloride
BIC—benzyl isocyanate
cDNA—complementary DNA
Ci—Curie
cm—centimeter
dATP—deoxyadenosine triphosphate
dCTP—deoxycytidine triphosphate
ddGTP—dideoxyguanosine triphosphate
ddNTP—dideoxynucleoside triphosphate
DIS—dimerization initiation site
dITP—deoxyinosine triphosphate
DMSO—dimethyl sulfoxide
DNA—deoxyribonucleic acid
dNTP—deoxynucleoside triphosphate
DTT—dithiothreitol
dTTP—deoxythymidine triphosphate
EDTA—ethylenediaminetetraacetic acid
HEPES—4-(2-hydroxyethyl)-1-piperazineethanesulfonic acid
HIV-1—human immunodeficiency virus type 1
hSHAPE—high throughput SHAPE
kcal—kilocalorie
KCl—potassium chloride
kDa—kilodalton(s)
L—liter
M—molar
mg—milligram
$MgCl_2$—magnesium chloride
mL—milliliter
mM—millimolar
MS—mass spectrometry
NaCl—sodium chloride
NMIA—N-methylisatoic anhydride
nmol—nanomole(s)
nt—nucleotide
NTP—nucleoside triphosphate
PAGE—polyacrylamide gel electrophoresis
PCR—polymerase chain reaction
pmol—picomole(s)
PEG—polyethylene glycol
RNA—ribonucleic acid
RT-PCR—reverse transcription polymerase chain reaction
SD—splice donor
SDS—sodium dodecyl sulfate
SHAPE—Selective 2'-Hydroxyl Acylation analyzed by Primer Extension
TAR—transactivation response element
TBE—Tris/borate/EDTA buffer
TE—Tris/EDTA
Tris—Tris(hydroxymethyl)aminomethane
VSV-G—Vesicular stomatitis virus glycoprotein
W—Watts
w/v—weight/volume
v/v—volume/volume
μM—micromolar
μg—microgram
° C.—degrees Celsius
%—percent
=—equal to
<—less than
>—greater than

BACKGROUND

RNA sequences fold back on themselves to form structures that are difficult to predict, especially if only a single sequence is known (Tinoco, I.; Bustamante, C. *J. Mol. Biol.* 1999, 293, 271-281.; Eddy, S. R. *Nature Biotechnology* 2004, 22, 1457-1458; Doshi, K. J.; Cannone, J. J.; Cobaugh, C. W.; Gutell, R. R. *BMC Bioinformatics* 2004, 5, 105). Current algorithms correctly predict 50-70% of known base pairs on average (R. D. Dowell, S. R. Eddy, BMC Bioinformatics 5, 71 (2004) and D. H. Mathews, D. H. Turner, Curr. Opin. Struct. Biol. 16, 270 (2006). Predicted secondary structure models achieving 50-70% accuracy tend to have regions wherein the overall topology differs significantly from the correct model, making it difficult or even impossible to develop robust biological hypotheses. Knowledge of which nucleotides are likely to be paired or single-stranded can significantly improve prediction accuracies (Wilkinson et al. (2006) *Nature Protocols* 1:1610-1616).

Methods for visualizing the secondary structures of RNA molecules have been reported, inclusive of, for example, Chetouani et al. (1997) *Nucleic Acids Res.* 25:3514-3522; Hogeweg et al. (1984) *Nucleic Acids Res.* 12:67-74; Matzura et al. (1996) *CABIOS* 12:247-249; Nussinov et al. (1978) *J. Appl. Math.* 35:68-82; and Osterburg et al. (1981) *Comput. Progr. Biomed.* 13:101-109. Particularly, local nucleotide structure can be monitored using well established approaches that involve treating an RNA with chemical and enzymatic reagents (Ehresmann et al. (1987) *Nucl Acids Res* 15:9109-9128). These methods are widely used and can give reasonable results, especially when multiple reagents are used together or when chemical modification information is interpreted in the context of phylogenetic covariation information (Barrick et al. (2004) *PNAS USA* 101:6421-6426). However, current reagents used to monitor local nucleotide structure react with a subset of RNA nucleotides. Therefore, multiple reagents must be used to comprehensively analyze all four nucleotides in a given RNA. In addition, reagents currently in use exhibit widely varying nucleotide and structural selectivities such that quantitative reactivity information cannot be readily compared for the different nucleotide bases or between reagents.

In addition, denaturing slab-gel electrophoresis is an available tool for separating nucleic acids by length. However, the production and imaging of gels is a labor-intensive task, and band resolution can be poor near the origin of separation. Software that quantifies gel electrophoresis images, such as SAFA (Das et al. (2005) *RNA* 11:344-54) typically cannot resolve and quantify more than 200 bands per separation at single nucleotide resolution.

Therefore, there is a need in the art for methods of analyzing secondary structures of RNA molecules, by which clear and compact graphic results can be obtained quickly, accurately, and at a low cost.

SUMMARY

The presently disclosed subject matter provides methods for detecting structural data in an RNA. In some embodiments, the methods comprise contacting an RNA containing 2'-O-adducts with a labeled primer; contacting an RNA containing no 2'-O-adducts with a labeled primer as a negative control; extending the primers to produce a library of cDNAs; analyzing the cDNAs; and producing output files comprising structural data for the RNA.

The RNA can present in a biological sample. The primers can be labeled with radioisotopes, fluorescent labels, heavy atoms, enzymatic labels a chemiluminescent group, a biotinyl group, a predetermined polypeptide epitope recognized by a secondary reporter, or combinations thereof. The analyzing can comprise separating, quantifying, sizing or combinations thereof. The analyzing can comprise extracting fluorescence or dye amount data as a function of elution time data. By way of example the cDNAs can be analyzed in a single column of a capillary electrophoresis instrument or in a microfluidics device.

In some embodiments peak area in traces for the RNA containing 2'-O-adducts and for the RNA containing no 2'-O-adducts versus nucleotide sequence can be calculated. The traces can be compared and aligned with the sequences of the RNAs. cDNAs comprising observing and accounting for that cDNAs generated by sequencing are one (1) nucleotide longer than corresponding positions in traces for the RNA containing 2'-O-adducts and for the RNA containing no 2'-O-adducts. Areas under each peak can be determined by performing a whole trace Gaussian-fit integration.

In some embodiments a dye separation matrix can be determined by detecting each label in one or more channels on a sequencer; and applying matrixing parameters simultaneously to the structural data to calculate dye amount versus elution time from fluorescence versus elution time. The matrixing parameters can be determined by using single dyes in independent sequencing capillary separations. Matrixing parameters can be determined for a dataset comprising (+) and (−) reagent traces, and sequencing traces. Peaks in the (+) and (−) sequencing traces can be aligned to the RNA sequence. In some embodiments the peaks can be aligned in the (+) and (−) sequencing traces to the RNA sequence by identifying peaks in the (+) and (−) traces; and matching the peaks with similar elution times in the sequencing traces to produce a series of peak positions as a function of nucleotide position to correlate peak intensities in the (+) and (−) traces and thereby align peaks in the (+) and (−) traces. Signal decay can be corrected in calculated peak intensities, in some embodiments by (a) correcting a single exponential decay using the equation: $y=ab^x+c$, wherein x is trace elution time; y is a correction factor for that time; and a, b, and c can be changed to better fit the data of individual data sets; and dividing each peak intensity in the (+) reagent data by the value of the equation.

In some embodiments the presently disclosed methods comprise calculating absolute nucleotide 2'-OH reactivity at single nucleotide resolution by matching calculated peak intensities corresponding to each nucleotide by multiplying data from the negative control by a factor, and calculating absolute reactivity at single nucleotide resolution by subtracting the data from the RNA containing 2'-O-adducts. The factor can be determined manually by visual inspection of the datasets. The factor can be calculated using statistical analysis.

In some embodiments the presently disclosed methods comprise normalizing, comparing, and joining different data sets containing RNA structural information. Outlying data points can be excluded by statistical analysis. Hyper-reactive nucleotides can be identified and excluded from normalization. Reactivity of generically reactive molecules can be averaged. The data sets to can be normalized to the average. The hyper-reactive nucleotides can be 2-4% of the most highly reactive nucleotides. The generically reactive nucleotides can be 8-10% of the nucleotides.

The structure can comprise a primer binding site, a protein binding site, a small molecule binding site, or a combination thereof. The structure can comprise a region of flexible nucleotides or nucleotides constrained by base pairing. The RNA structure can be analyzed in the presence and absence of a primer, a protein, a small molecule or a combination thereof to identify a primer binding site, a protein binding site, a small molecule binding site, or a combination thereof.

Methods of forming a covalent ribose 2'-O-adduct with RNA are also provided herein, as are covalent ribose 2'-O-adducts with RNA formed by the methods. In some embodiments, the method comprises contacting an electrophile with RNA wherein the electrophile selectively modifies unconstrained nucleotides in the RNA to form a covalent ribose 2'-O-adduct. The electrophile can be selected from the group included but not limited to an isatoic anhydride derivative, a benzoyl cyanide derivative, a benzoyl chloride derivative, a phthalic anhydride derivative, a benzyl isocyanate derivative, and combinations thereof. The isatoic anhydride derivative can comprise 1-methyl-7-nitroisatoic anhydride (1M7). The benzoyl cyanide derivative can be selected from the group including but not limited to benzoyl cyanide (BC), 3-carboxybenzoyl cyanide (3-CBC), 4-carboxybenzoyl cyanide (4-CBC), 3-aminomethylbenzoyl cyanide (3-AMBC), 4-aminomethylbenzoyl cyanide, and combinations thereof. The benzoyl chloride derivative can comprise benzoyl chloride (BCl). The phthalic anhydride derivative can comprise 4-nitrophthalic anhydride (4NPA). The benzyl isocyanate derivative can comprise benzyl isocyanate (BIC).

Also provided herein are covalent ribose 2'-O-adducts. In some embodiments the covalent ribose 2'-O-adduct comprise RNA and an electrophile bound at the 2'-O— position of one or more unconstrained nucleotides in the RNA. The electrophile can be selected from the group included but not limited to an isatoic anhydride derivative, a benzoyl cyanide derivative, a benzoyl chloride derivative, a phthalic anhydride derivative, a benzyl isocyanate derivative, and combinations thereof.

Also provided herein are electrophilic compositions for modifying RNA to form a covalent ribose 2'-O-adduct, comprising an isatoic anhydride derivative, a benzoyl cyanide derivative, a benzoyl chloride derivative, a phthalic anhydride derivative, a benzyl isocyanate derivative, and combinations thereof.

Also provided herein are methods for producing a graphical indication of at least one of structure and reactivity of an RNA sample. In some embodiments, the methods comprise: receiving raw elution RNA trace data produced by a DNA sequencer for an RNA sample; processing the raw elution RNA trace data to produce a graphical indication of at least one of structure and reactivity of the RNA sample; and displaying the graphical indication. Processing the raw elution RNA trace data can include applying at least one DNA sequencing processing step to channels of the RNA trace data. Processing the raw elution RNA trace data can include determining location and intensity of peaks of the RNA trace data to quantify nucleotide flexibility.

The subject matter described herein for high-throughput RNA structure analysis can be implemented using a computer program product comprising computer executable instructions embodied in a computer-readable medium. Exemplary computer-readable media suitable for implementing the subject matter described herein include chip memory devices, disc memory devices, programmable logic devices, and application specific integrated circuits. In addition, a computer program product that implements the subject matter described herein can be located on a single device or computing platform or can be distributed across multiple devices or computing platforms. Thus, the subject matter described herein can include a set of computer instructions, that when executed by a computer, performs a specific function for high-throughput RNA structure analysis.

It is an object of the presently disclosed subject matter to provide methods for high-throughput RNA structure analysis.

An object of the presently disclosed subject matter having been stated hereinabove, and which is achieved in whole or in part by the presently disclosed subject matter, other objects will become evident as the description proceeds when taken in connection with the accompanying drawings as best described herein below.

BRIEF DESCRIPTION OF THE DRAWINGS

FIG. 3b is a graph of band intensities indicating that SHAPE reactivity is significantly higher in the (+) NMIA reaction as compared to the (−) no reagent control.

FIG. 3c is a graph illustrating absolute SHAPE reactivities at almost every position within the RNA obtained by subtracting the (−) control intensities from the (+) NMIA intensities.

FIG. 3d is a schematic representation of a superposition of absolute band intensities on a secondary structure model for the tRNAAsp construct (SEQ ID NO: 5) to yield information regarding the pattern of base pairing and the formation of non-canonical tertiary interactions in the RNA.

DETAILED DESCRIPTION

Figure 1A:
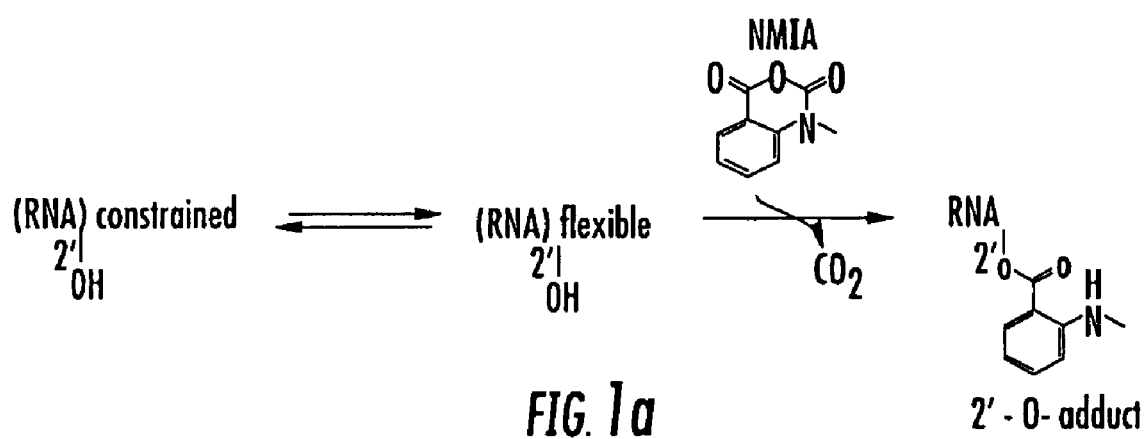
FIG. 1a is a chemical representation illustrating that hydroxyl-selective electrophiles, such as NMIA form stable 2'-O-adducts.

The details of one or more embodiments of the presently disclosed subject matter are set forth in the accompanying description below. Other features, objects, and advantages of the presently disclosed subject matter will be apparent from the detailed description, Appendix, and claims. All publications, patent applications, patents, and other references mentioned herein are incorporated by reference in their entirety. Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. In case of conflict, the present specification, including definitions, will control.

I. GENERAL CONSIDERATIONS

The biological function of RNA is mediated by its structure. mRNA is generally thought of as a linear molecule which contains the information for directing protein synthesis within the sequence of ribonucleotides. Studies have revealed a number of secondary and tertiary structures in mRNA which are important for its function (Tinoco et al. (1987) *Symp. Quant. Biol.* 52:135). Secondary structural elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure.

Very little is known about the precise three dimensional structure of RNA. However, there have been a number of research efforts which have shown that RNA structures, including single stranded, secondary and tertiary structures, have important biological functions beyond simply encoding the information to make proteins in linear sequences (Resnekov et al. (1989) *J. Biol. Chem.* 264:9953; Tinoco et al. (1987) *Symp. Quant. Biol.* 52:135; Tuerk et al. (1988) *PNAS USA* 85:1364; and Larson et al. (1987) *Mol. Cel. Biochem.* 74:5).

For example, the HIV-1 RNA genome participates in multiple, pivotal, stages of the viral infectivity cycle. It serves as a template for synthesis of viral proteins, forms intermolecular dimer interactions that direct packaging and enable recombination between two RNA strands, base pairs with the tRNA (lys3) molecule that primes proviral DNA synthesis, and binds essential regulatory and cofactor proteins (Coffin et al. (1997) *Retroviruses*, Cold Spring Harbor Press, Cold Spring Harbor, N.Y.; Frankel et al. (1998) *Ann Rev Biochem* 67:1-25). The HIV genome represents a compelling target for antiviral therapies because it is both the largest component of the virus and conserved interactions with proteins and other RNAs are critical for infectivity. However, current understanding of HIV genomic RNA structure, and of the structures of virtually all long viral and cellular RNAs, has been limited to highly focused analyses of short pieces of RNA. Accordingly, there is a need in the art for an approach for analysis of the global architecture of RNA to analyze the structure of intact HIV-1 genomes inside infectious virions, as a representative viral target.

As disclosed herein, the presently disclosed Selective 2'-Hydroxyl Acylation analyzed by Primer Extension (SHAPE) method allows the determination of quantitative reactivity information at every nucleotide position. Several signal-processing innovations are provided herein. In some embodiments, using a modified version of a data processing program, such as, for example, BaseFinder (Giddings et al. (1998) *Genome Res* 8:644-645) the (+) and (−) SHAPE reagent traces to the RNA sequence, (ii) the (+) and (−) SHAPE reagent peaks are integrated, (iii) signal decay is corrected, and (iv) SHAPE reactivities are normalized to a universal scale. These steps can produce a single-nucleotide resolution view of RNA flexibility at all nucleotides.

Figure 8:
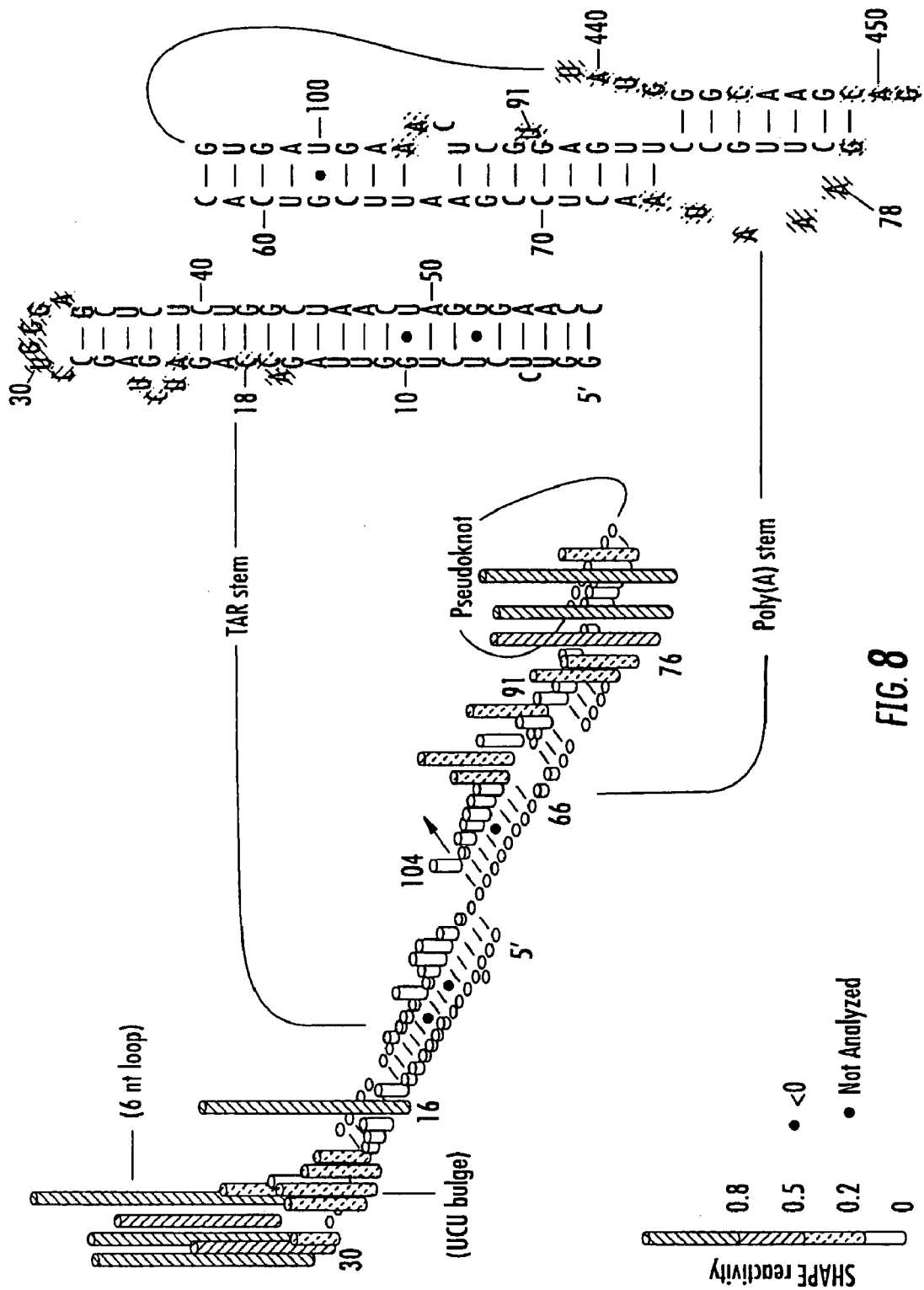
FIG. 8 is a bar plot and schematic representation showing absolute SHAPE reactivities, superimposed on the well-characterized TAR and Poly(A) stem loops (nts 1-104; SEQ ID NO: 8), which show that SHAPE information is exactly consistent with the consensus secondary structure for this region such that nucleotides in loops are reactive whereas base paired nucleotides are unreactive. The sequence corresponding to nt 439-451 (SEQ ID NO: 9) is also shown.

Highly reactive nucleotides have similar SHAPE reactivities, independent of whether they lie at the 5' or 3' end of the RNA. Additionally, SHAPE reactivity is largely independent of nucleotide identity. Absolute SHAPE reactivities, superimposed on the well-characterized TAR and Poly(A) stem loops (nts 1-104), show that SHAPE information is exactly consistent with the consensus secondary structure for this region such that nucleotides in loops are reactive whereas base paired nucleotides are unreactive. See FIG. 8. Notably, SHAPE reactivities accurately report fine-scale structural differences. For example, nucleotides in the UCU bulge show intermediate reactivities, consistent with NMR studies (Puglisi et al. (1992) *Science* 257:76-80) that indicate that these nucleotides in the TAR stem are partially stacked. Further, the high throughput Selective 2'-Hydroxyl Acylation analyzed by Primer Extension (hSHAPE) data obtained from a single high-throughput, multiplex experiment analyzed on a DNA sequencer are consistent with those from previous qualitative structural mapping studies using multiple chemical and enzyme reagents, each of which analyzed a subset of the nucleotides analyzable by hSHAPE.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

II. SHAPE CHEMISTRY

SHAPE chemistry is based at least in part on the observation that the nucleophilicity of the RNA ribose 2'-position is sensitive to the electronic influence of the adjacent 3'-phosphodiester group. Unconstrained nucleotides sample more conformations that enhance the nucleophilicity of the 2'-hydroxyl group than do base paired or otherwise constrained nucleotides. Therefore, hydroxyl-selective electrophiles, such as but not limited to N-methylisatoic anhydride (NMIA), form stable 2'-O-adducts more rapidly with flexible RNA nucleotides (FIG. 1a). Local nucleotide flexibility can be interrogated simultaneously at all positions in an RNA in a single experiment because all RNA nucleotides (except a few cellular RNAs carrying post-transcriptional modifications) have a 2'-hydroxyl group. Absolute SHAPE reactivities can be compared across all positions in an RNA because 2'-hydroxyl reactivity is insensitive to base identity. It is also possible that a nucleotide can be reactive because it is constrained in a conformation that enhances the nucleophilicity of a specific 2'-hydroxyl. This class of nucleotide is expected to be rare, would involve a non-canonical local geometry, and would be scored correctly as an unpaired position.

The presently disclosed subject matter provides in some embodiments methods for detecting structural data in an RNA by interrogating structural constraints in RNA of arbitrary length and structural complexity. In some embodiments, the methods comprise annealing an RNA containing 2'-O-adducts with a labeled primer; annealing an RNA containing no 2'-O-adducts with a labeled primer as a negative control; extending the primers to produce a library of cDNAs; analyzing the cDNAs; and producing output files comprising structural data for the RNA.

The RNA can be present in a biological sample. The primers can be labeled with radioisotopes, fluorescent labels, heavy atoms, enzymatic labels, a chemiluminescent group, a biotinyl group, a predetermined polypeptide epitope recognized by a secondary reporter, or combinations thereof. The analyzing can comprise separating, quantifying, sizing or combinations thereof. The analyzing can comprise extracting fluorescence or dye amount data as a function of elution time data, which are called traces. By way of example the cDNAs can be analyzed in a single column of a capillary electrophoresis instrument or in a microfluidics device.

In some embodiments peak area in traces for the RNA containing 2'-O-adducts and for the RNA containing no 2'-O-adducts versus nucleotide sequence can be calculated. The traces can be compared and aligned with the sequences of the RNAs. Traces observing and accounting for those cDNAs generated by sequencing are one (1) nucleotide longer than corresponding positions in traces for the RNA containing 2'-O-adducts and for the RNA containing no 2'-O-adducts. Areas under each peak can be determined by performing a whole trace Gaussian-fit integration.

Thus provided herein in some embodiments are methods for forming covalent ribose 2'-O-adducts with RNA in complex biological solutions. In some embodiments, an electrophile, such as but not limited to N-methylisatoic anhydride (NMIA) is dissolved in an anhydrous, polar, aprotic solvent such as DMSO. The reagent-solvent solution is added to a complex biological solution containing RNA. The solution can contain different concentrations and amounts of proteins, cells, viruses, lipids, mono- and polysaccharides, amino acids, nucleotides, DNA, and different salts and metabolites. The concentration of the electrophile can be adjusted to achieve the desired degree of modification in the RNA. The electrophile has the potential to react with all free hydroxyl groups in solution, producing ribose 2'-O-adducts on RNA. Further, the electrophile can selectively modify unpaired, or otherwise unconstrained nucleotides in the RNA.

The term "aprotic solvent" refers to a solvent molecule which can neither accept nor donate a proton. Typical aprotic solvents include, but are not limited to, acetone, acetonitrile, benzene, butanone, butyronitrile, carbon tetrachloride, chlorobenzene, chloroform, 1,2-dichloroethane, dichloromethane, diethyl ether, dimethylacetamide, N,N-dimethylformamide (DMF), dimethylsulfoxide (DMSO), 1,4-dioxane, ethyl acetate, ethylene glycol dimethyl ether, hexane, N-methylpyrrolidone, pyridine, tetrahydrofuran (THF), and toluene. Certain aprotic solvents are polar solvents. Examples of polar aprotic solvents include, but are not limited to, acetone, acetonitrile, butanone, N,N-dimethylformamide, and dimethylsulfoxide. Certain aprotic solvents are non-polar solvents. Examples of nonpolar, aprotic solvents include, but are not limited to, diethyl ether, aliphatic hydrocarbons, such as hexane, aromatic hydrocarbons, such as benzene and toluene, and symmetrical halogenated hydrocarbons, such as carbon tetrachloride.

Appropriate electrophiles react selectively with flexible RNA nucleotides at the ribose 2'-hydroxyl group as depicted in FIG. 1a and as per Scheme 1 below:

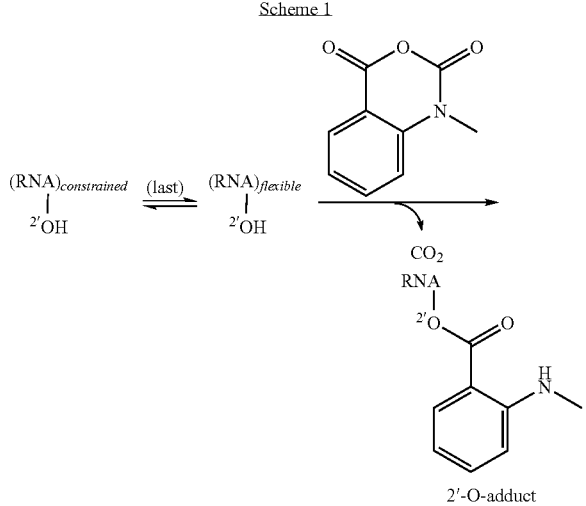

Scheme 1

The RNA can be exposed to the electrophile at a concentration that yields sparse RNA modification to form 2'-O-adducts, which can be detected by the ability to inhibit primer extension by reverse transcriptase. All RNA sites can be interrogated in a single experiment because the chemistry targets the generic reactivity of the 2'-hydroxyl group. In some embodiments, a control extension reaction omitting the electrophile to assess background, as well as dideoxy sequencing extensions to assign nucleotide positions, can be performed in parallel. These combined steps are called selective 2'-hydroxyl acylation analyzed by primer extension, or SHAPE.

The number of nucleotides interrogated in a single SHAPE experiment depends not only on the detection and resolution of separation technology used, but also on the nature of RNA modification. Given reaction conditions, there is a length where nearly all RNA molecules have at least one modification. As primer extension reaches these lengths, the amount of extending cDNA decreases, which attenuates experimental signal. Adjusting conditions to decrease modification yield can increase readlength. However, lowering reagent yield can also decrease the measured signal for each cDNA length. Given these considerations, a preferred maximum length of a single SHAPE read is probably about 1 kilobase of RNA.

To create high-throughput SHAPE (hSHAPE), one or more extension reactions are conducted using a labeled primer. The primers can be labeled according to any technique known in the art, including but not limited to, radiolabeling, fluorescent labeling, enzymatic labeling, and sequence tagging. Thus provided herein are methods for detecting covalent ribose 2'-O-adducts in RNA using fluorescently labeled DNA or RNA primers. In some embodiments, a DNA or RNA primer, labeled with a 5'-fluorescent label, is annealed to the 3'-end of an RNA containing 2'-O-adducts. The DNA or RNA primers can anneal to any location in the target RNA; thus making it possible to analyze an entire RNA or a part of a long RNA. Long structural reads can be created by using overlapping reads with primers that anneal at regular intervals. The data from individual reads is then combined to generate a comprehensive analysis of the structure of RNAs of any length.

The primer is extended using a reverse transcriptase reaction with RNA as the template. The end product is a library of cDNAs whose length and amount correspond to position and degree of structure-sensitive modification in an RNA ((+) reagent experiment). The DNA or RNA primer is extended on an RNA subject to a mock modification reaction in which the electrophile was omitted. The same primer sequence is used but a different fluorophore is linked to the 5'-end of the primer ((−) reagent control).

To locate positions of modification, RNA or DNA primers of the same sequence but linked with additional different fluorophores are used to initiate primer extension on an RNA or DNA template in the presence of dideoxynucleotide triphosphate. The cDNAs from each extension can be separated, quantified, and/or sized in a single column of a capillary electrophoresis instrument or in a microfluidics device. Data including fluorescence or dye amount as a function of elution time can be extracted from output files. This data can contain both sequence and structural information for an RNA.

For analysis of complex mixtures containing less than 1 pmol of target RNA, the following exemplary procedure can be used to amplify signal: a DNA primer of specific length and sequence is ligated to the 3'-end of the extended cDNA primers. Forward (additional fluorescently labeled primer described herein) and reverse (compliment of the ligated DNA sequence) primers can be used in a quantitative PCR-type experiment to amplify the extended cDNA in a quantitative manner. Therefore, the length and amount of the DNAs produced reflects the position and degree of modification, but amplified DNA length is offset by the specific length of the ligated DNA.

Also disclosed herein are methods for calculating dye separation matrix for an RNA structure analysis experiment. Each fluorescent dye can be detected in multiple channels on a DNA sequencer. To calculate dye amount versus elution time from fluorescence versus elution time, matrix parameters can be applied simultaneously to the data. Matrixing parameters can be determined by using single dyes in independent sequencing capillary separations. A multi-component analysis can be used to determine matrix parameters for a complete dataset including (+) and (−) reagent traces as well as sequencing traces.

Also disclosed herein are methods for aligning (+), (−) and sequencing traces such that corresponding peaks all have almost the same elution time. Alignment parameters can be developed by using DNA sequencing experiments with the same primer sequence and fluorophore set used in a structure analysis experiment. The sequencing ladders and elution times for each dye are then compared to locate and align corresponding peaks. The parameters for alignment can applied to an entire experiment comprising a (+), (−) reagent, and sequencing extensions to make corresponding peaks align at specific elution times.

Also provided herein are methods for aligning peaks in the (+) and (−) sequencing traces to the RNA sequence. Peaks in the (+) and (−) traces are identified and matched to peaks with similar elution times in the sequencing traces, or vice versa. A user can modify peak identification to more precisely match reagent peaks with sequence. The result can be a series of peak positions as a function of nucleotide position, where peak intensity in the (+) and (−) traces can be correlated to nucleotide flexibility. In some embodiments, the primer can be labeled with a radionuclide label, including but not limited to, a radionuclide label selected from the group consisting of $^{32}$phosphorus, phosphorus, $^{35}$sulfur, $^{18}$-fluorine, $^{64}$copper, $^{65}$copper, $^{67}$gallium, $^{68}$gallium, $^{77}$bromine, $^{80m}$bromine, $^{95}$ruthenium, $^{97}$ruthenium, $^{103}$ruthenium, $^{105}$ruthenium, $^{99m}$technetium, $^{107}$mercury, $^{203}$mercury, $^{123}$iodine, $^{124}$iodine, $^{125}$iodine, $^{126}$iodine, $^{131}$iodine, $^{133}$iodine, $^{111}$indium, $^{113}$mindium, $^{99m}$rhenium, $^{105}$rhenium, $^{101}$rhenium, $^{186}$rhenium, $^{188}$rhenium, $^{121m}$tellurium, $^{122m}$tellurium, $^{125m}$tellurium, $^{165}$thulium, $^{167}$thulium, $^{168}$thulium, and nitride or oxide forms derived there from, as well as any combinations of any of the foregoing.

In some embodiments, the primer can be labeled with a color-coded fluorophore and the resulting cDNAs resolved in one multi-fluorescence experiment. Fluorescent probes that can be utilized include, but are not limited to, fluorescein isothiocyanate; fluorescein dichlorotriazine and fluorinated analogs of fluorescein; naphthofluorescein carboxylic acid and its succinimidyl ester; carboxyrhodamine 6G; pyridyloxazole derivatives; Cy2, 3, 3.5, 5, 5.5, and 7; phycoerythrin; phycoerythrin-Cy conjugates; fluorescent species of succinimidyl esters, carboxylic acids, isothiocyanates, sulfonyl chlorides, and dansyl chlorides, including propionic acid succinimidyl esters, and pentanoic acid succinimidyl esters; succinimidyl esters of carboxytetramethylrhodamine; rhodamine Red-X succinimidyl ester; Texas Red sulfonyl chloride; Texas Red-X succinimidyl ester; Texas Red-X sodium tetrafluorophenol ester; Red-X; Texas Red dyes; tetramethylrhodamine; lissamine rhodamine B; tetramethylrhodamine; tetramethylrhodamine isothiocyanate; naphthofluoresceins; coumarin derivatives (e.g., hydroxycoumarin, aminocoumarin, and methoxycoumarin); pyrenes; pyridyloxazole derivatives; dapoxyl dyes; Cascade Blue and Yellow dyes; benzofuran isothiocyanates; ABI sequencing dyes (NED, SAM, JOE, TAMRA, ROX, HEX, 6-FAM, VIC, TET, and LIZ); WellRED dyes (WellRED1, WellRED2, WellRED3, and WellRED4); sodium tetrafluorophenols; 4,4-difluoro-4-bora-3a,4a-diaza-s-indacene; Alexa fluors (e.g., 350, 430, 488, 532, 546, 555, 568, 594, 633, 647, 660, 680, 700, and 750); green fluorescent protein; and yellow fluorescent protein. The peak excitation and emission wavelengths can vary for these compounds and selection of a particular fluorescent probe for a particular application can be made in part based on excitation and/or emission wavelengths. In some embodiments, the multifluorescence run can be through automated capillary electrophoresis. hSHAPE can be used, for example, to analyze and combine information from about 300 nucleotide segments to determine the structure of a 976-nt RNA corresponding to the 5' end of the HIV-1 RNA genome.

The hSHAPE profile can report RNA structural information through the amplitudes of the (+) and (−) electrophile (e.g., NMIA) reagent traces. In some embodiments, peaks with little or no reactivity in the (+) trace correspond to RNA nucleotides constrained by base pairing or other interactions. In comparison, tall peaks indicate high reactivity and correspond to conformationally flexible positions.

Figure 1B:
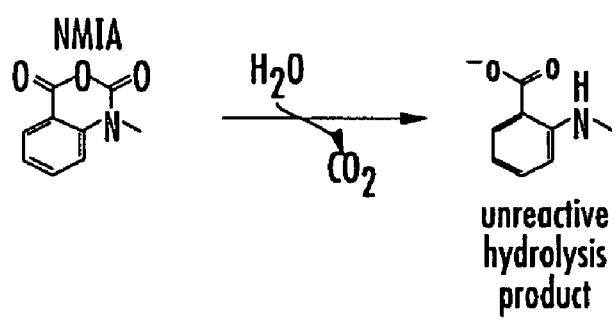
FIG. 1b is a chemical representation illustrating that the NMIA reagent is consumed by a competing hydrolysis reaction.

In some embodiments, the electrophile is consumed by a competing hydrolysis reaction (FIG. 1b) that can advantageously cause the reaction to be self-limiting. Thus, only the initial electrophile concentration need be adjusted to achieve an appropriate level of 2'-O-adduct formation; no explicit quench step is required. Once the reaction is complete, a 5'-radiolabeled cDNA can be annealed to the modified RNA, and sites of 2'-O-adduct formation are identified as stops to primer extension by reverse transcriptase. cDNAs can be separated by any of a variety of methods as would be readily understood to one of ordinary skill in the art, including but not limited to, standard high-resolution gel electrophoresis. Absolute electrophile reactivity at each nucleotide can then be determined by comparing band intensities from the modification reaction to a control omitting electrophile. One or more dideoxy sequencing lanes are used to assign bands within the electrophile reaction and control lanes. In some embodiments, structural information can be read for about 100-150 nucleotides 5' to the DNA primer.

A SHAPE experiment can be carried out on minimal quantities of target reagent, such as 34 pmol of RNA. 2 pmol can be used in the SHAPE chemistry itself and 1 pmol can be used for each sequencing experiment used for band assignment. In some embodiments, one or more sequencing experiments can be sufficient. RNAs of any length are appropriate substrates for SHAPE. The RNA is desirably free of transcriptional modifications or unusually stable secondary structures that could prevent its functioning as a template for primer extension. Electrophile modification works well under a wide variety of solution conditions, ionic strength, and temperatures, such as but not limited to, 0-200 mM monovalent ion (NaCl, KCl or potassium acetate), 0-40 mM $MgCl_2$, and 20-75° C.

Continuing, the RNA can be modified in the presence of protein or other small and large biological ligands. Solution components that react directly with the electrophile as well as organic co-solvents, including for example formamide and DMSO, can be well tolerated but can require that reagent concentrations be adjusted. Because electrophile reactivity can be strongly dependent on pH, the pH can be maintained at any suitable range, such as but not limited to pH 7.5 to 8.0. The dynamic range that differentiates the most reactive (flexible) and least reactive (constrained) nucleotides typically spans a factor of 20-50.

A SHAPE experiment can obtain constraints sufficient to establish or confirm the secondary structure model of an arbitrary RNA. SHAPE chemistry can be suited to map structural variations among homologous RNAs and the structural consequences of a suite of mutations. Other applications of SHAPE include monitoring thermal melting of an RNA at single nucleotide resolution, identifying regions of an RNA that do not fold to a single well-defined structure, mapping equilibrium conformational changes that accompany an RNA folding reaction, identifying protein binding sites, and identifying sites that can be bound by (for example, small molecule, siRNA, or antisense) drugs.

III. SHAPE ELECTROPHILES

As disclosed hereinabove, SHAPE chemistry takes advantage of the discovery that the nucleophilic reactivity of a ribose 2'-hydroxyl group is gated by local nucleotide flexibility. At nucleotides constrained by base pairing or tertiary interactions, the 3'-phosphodiester anion and other interactions reduce reactivity of the 2'-hydroxyl. In contrast, flexible positions preferentially adopt conformations that react with an electrophile, including but not limited to NMIA, to form a 2'-O-adduct. By way of example, NMIA reacts generically with all four nucleotides and the reagent undergoes a parallel, self-inactivating, hydrolysis reaction.

However, NMIA has relatively low reactivity and can require tens of minutes to react to completion. Thus, fast acting reagents for SHAPE chemistry have been designed. The structural constraints obtained using these reagents allow the secondary and tertiary structure of a large RNA to be assessed with high accuracy.

Accordingly, alternative SHAPE reagents have been developed. The SHAPE reagents include, but are not limited to, isatoic anhydride derivatives, benzoyl cyanide derivatives, benzoyl chloride derivatives, phthalic anhydride derivatives, and benzyl isocyanate derivatives. Novel 2'-O-adducts comprising the SHAPE reagents are also provided. The following compounds can be synthesized employing techniques disclosed herein and in accordance with techniques that would be apparent to one of ordinary skill in the art upon a review of the present disclosure.

III.A. Isatoic Anhydride Derivatives

In some embodiments, the isatoic anhydride derivatives suitable for use with the SHAPE methodology are represented below, wherein X and Y can be any functional group, and the reactive carbon center is circled:

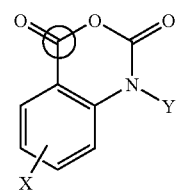

An adduct formed between an isatoic anhydride derivative and a RNA nucleotide can have the structure:

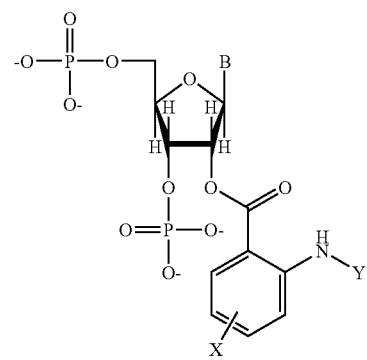

In some embodiments, the isatoic anhydride derivative can be 1-methyl-7-nitroisatoic anhydride (1M7):

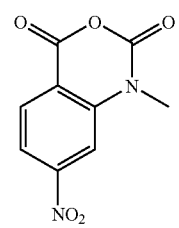

III.B. Benzoyl Cyanide Derivatives

In some embodiments, the benzoyl cyanide derivatives are represented below, wherein X can be any functional group (representative functional groups are disclosed herein below), and the reactive carbon center is circled:

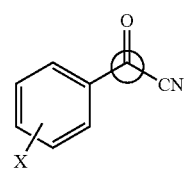

An adduct formed between a benzoyl cyanide derivative and a RNA nucleotide can have the structure:

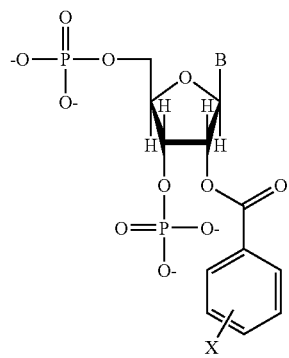

In some embodiments, the benzoyl cyanide derivative can comprise benzoyl cyanide (BC):

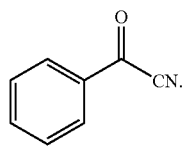

In some embodiments, the benzoyl cyanide derivative can comprise 3-carboxybenzoyl cyanide (3-CBC):

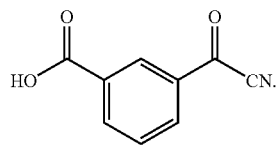

In some embodiments, the benzoyl cyanide derivative can comprise 4-carboxybenzoyl cyanide (4-CBC):

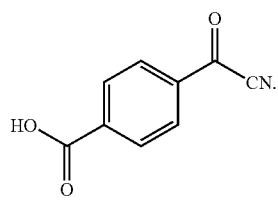

In some embodiments, the benzoyl cyanide derivative can comprise 3-aminomethylbenzoyl cyanide (3-AMBC):

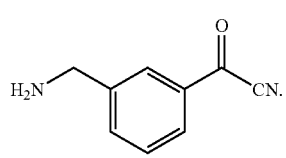

In some embodiments, the benzoyl cyanide derivative can comprise 4-aminomethylbenzoyl cyanide:

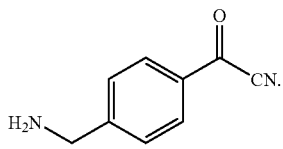

III.C. Benzoyl Chloride Derivatives

In some embodiments, the benzoyl chloride derivatives are represented below, wherein X can be any functional group, and the reactive carbon center is circled:

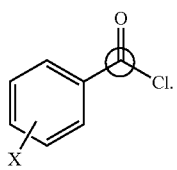

An adduct formed between a benzoyl chloride derivative and a RNA nucleotide can have the structure:

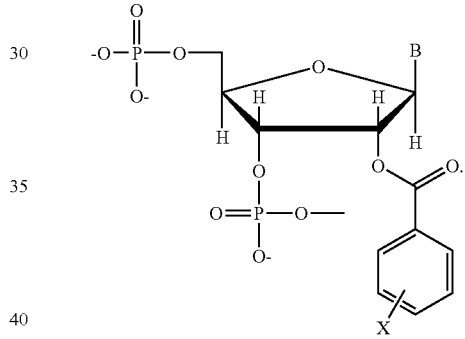

In some embodiments, the benzoyl chloride derivative can comprise benzoyl chloride (BCl):

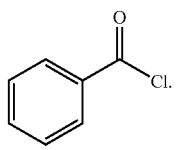

III.D. Phthalic Anhydride Derivatives

In some embodiments, the phthalic anhydride derivatives are represented below, wherein X can be any functional group, and the reactive carbon center is circled:

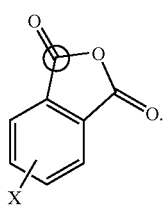

An adduct formed between a phthalic anhydride derivative and a RNA nucleotide can have the structure:

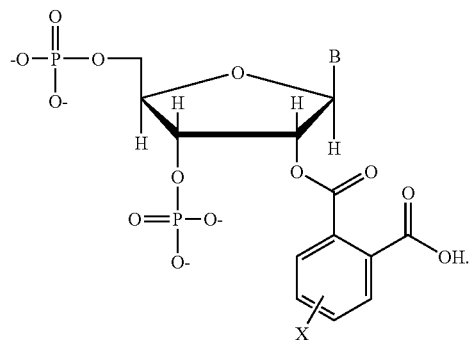

In some embodiments, the phthalic anhydride derivative can comprise phthalic anhydride (PA):

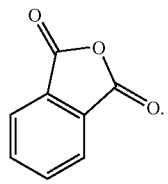

In some embodiments, the phthalic anhydride derivative can comprise 4-nitrophthalic anhydride (4NPA):

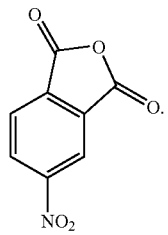

III.E. Benzyl Isocyanate Derivatives

In some embodiments, the benzyl isocyanate derivatives are represented below, wherein X can be any functional group, and the reactive carbon center is circled:

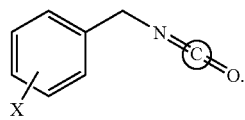

An adduct formed between a benzyl isocyanate derivative and a RNA nucleotide can have the structure:

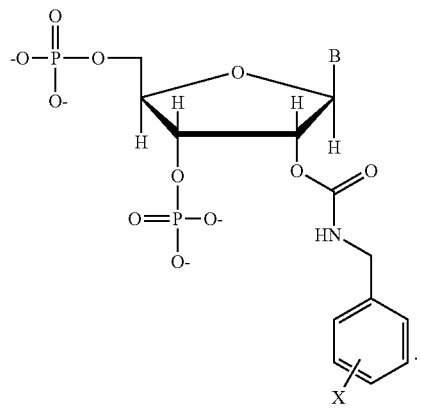

In some embodiments, the benzyl isocyanate derivative can comprise benzyl isocyanate (BIC):

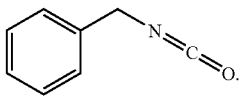

In some embodiments, the X substituent of the isatoic anhydride, benzoyl cyanide, benzoyl chloride, phthalic anhydride, or benzyl isocyanate derivative can be a functional group including, but not limited to, alkyl, substituted alkyl, cycloalkyl, aryl, substituted aryl, heteroaryl, alkoxyl, aryloxyl, aralkyl, aralkoxyl, dialkylamino, nitro, carboxyl, halo, acyl, hydroxyalkyl, aminoalkyl. In some embodiments, Y can be a functional group including, but not limited to, alkyl, substituted alkyl, cycloalkyl, aryl, substituted aryl, heteroaryl, hydroxyalkyl, and aminoalkyl.

A named "X", "Y", or in some cases "R" functional group will generally have the structure that is recognized in the art as corresponding to a group having that name, unless specified otherwise herein. For the purposes of illustration, certain representative named "X", "Y", or in some cases "R" functional groups are defined below. These definitions are intended to supplement and illustrate, not preclude, the definitions that would be apparent to one of ordinary skill in the art upon review of the present disclosure.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

A structure represented generally by a formula such as:

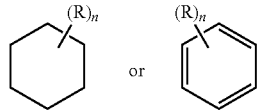

as used herein refers to a ring structure; for example, but not limited to a 3-carbon, a 4-carbon, a 5-carbon, a 6-carbon, and the like, aliphatic and/or aromatic cyclic compound comprising a substituent R group, wherein the R group can be present or absent, and when present, one or more R groups can each be substituted on one or more available carbon atoms of the ring structure. The presence or absence of the R group and number of R groups is determined by the value of the integer n. Each R group, if more than one, is substituted on an available carbon of the ring structure rather than on another R group. For example, the structure:

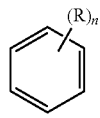

wherein n is an integer from 0 to 2 comprises compound groups including, but not limited to:

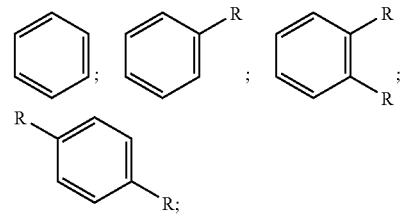

and the like.

In some embodiments, the compounds described by the presently disclosed subject matter contain a linking group. As used herein, the term "linking group" comprises a chemical moiety, such as a furanyl, phenylene, thienyl, and pyrrolyl radical, which is bonded to two or more other chemical moieties, in particular aryl groups, to form a stable structure.

When a named atom of an aromatic ring or a heterocyclic aromatic ring is defined as being "absent," the named atom is replaced by a direct bond. When the linking group or spacer group is defined as being absent, the linking group or spacer group is replaced by a direct bond.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$O—); and ethylenedioxyl (—O—$(CH_2)_2$—O—). An alkylene group can have about 2 to about 3 carbon atoms and can further have 6-20 carbons.

As used herein, the term "acyl" refers to an organic carboxylic acid group wherein the —OH of the carboxyl group has been replaced with another substituent (i.e., as represented by RCO—, wherein R is an alkyl or an aryl group as defined herein). As such, the term "acyl" specifically includes arylacyl groups, such as an acetylfuran and a phenacyl group. Specific examples of acyl groups include acetyl and benzoyl.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalkyl" can be used interchangably with "alkoxyl".

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl.

"Dialkylamino" refers to an —NRR' group wherein each of R and R' is independently an alkyl group and/or a substituted alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group wherein one of R and R' is hydrogen and the other of R and R' is alkyl and/or substituted alkyl as previously described.

"Dialkylcarbamoyl" refers to a R'RN—CO— group wherein each of R and R' is independently alkyl and/or substituted alkyl as previously described.

"Acyloxyl" refers to an acyl-O— group wherein acyl is as previously described.

"Acylamino" refers to an acyl-NH— group wherein acyl is as previously described.

The term "amino" refers to the —$NH_2$ group.

The term "carbonyl" refers to the —(C=O)— group.

The term "carboxyl" refers to the —COOH group.

The terms "halo", "halide", or "halogen" as used herein refer to fluoro, chloro, bromo, and iodo groups.

The term "hydroxyl" refers to the —OH group.

The term "hydroxyalkyl" refers to an alkyl group substituted with an —OH group.

The term "aminoalkyl" refers to an alkyl group substituted with an —$NH_2$ group. Thus, an "aminoalkyl" group can be a $NH_2(CH_2)_n$ group, wherein n is an integer from 1 to 6 (i.e., 1, 2, 3, 4, 5, or 6).

The term "mercapto" refers to the —SH group.

The term "oxo" refers to a compound described previously herein wherein a carbon atom is replaced by an oxygen atom.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

When the term "independently selected" is used, the substituents being referred to (e.g., R groups, such as groups $R_1$ and $R_2$, or groups X and Y), can be identical or different. For example, both X and Y can be substituted alkyls, or X can be hydrogen and Y can be a substituted alkyl, or vice versa, and the like.

IV. RNA DESIGN

Because SHAPE reactivities can be assessed in one or more primer extension reactions, information can be lost at both the 5' end and near the primer binding site of an RNA. Typically, adduct formation at the 10-20 nucleotides adjacent to the primer binding site is difficult to quantify due to the presence of cDNA fragments that reflect pausing or non-templated extension by the reverse transcriptase (RT) enzyme during the initiation phase of primer extension. The 8-10 positions at the 5' end of the RNA can be difficult to visualize due to the presence of an abundant full-length extension product.

To monitor SHAPE reactivities at the 5' and 3' ends of a sequence of interest, the RNA can be embedded within a larger fragment of the native sequence or placed between strongly folding RNA sequences that contain a unique primer binding site. In some embodiments, a structure cassette can be designed that contains 5' and 3' flanking sequences of nucleotides to allow all positions within the RNA of interest to be evaluated in any separation technique affording nucleotide resolution, such as but not limited to a sequencing gel, capillary electrophoresis, and the like. In some embodiments, both 5' and 3' extensions can fold into stable hairpin structures that do not to interfere with folding of diverse internal RNAs. The primer binding site of the cassette can efficiently bind to a cDNA primer. The sequence of any 5' and 3' structure cassette elements can be checked to ensure that they are not prone to forming stable base pairing interactions with the internal sequence.

V. RNA FOLDING

The presently disclosed SHAPE experiment can be performed with RNA generated by methods including but not limited to in vitro transcription and RNA generated in cells and viruses. In some embodiments, the RNAs can be purified by denaturing gel electrophoresis and renatured to achieve a biologically relevant conformation. Further, any procedure that folds the RNA to a desired conformation at a desired pH (e.g., about pH 8) can be substituted. The RNA can be first heated and snap cooled in a low ionic strength buffer to eliminate multimeric forms. A folding solution (representative embodiments disclosed in the Example herein below) can then be added to allow the RNA to achieve an appropriate conformation and to prepare it for structure-sensitive probing with an electrophile. In some embodiments, the RNA can be folded in a single reaction and later separated into (+) and (−) electrophile reactions. In some embodiments, RNA is not natively folded before modification. Modification can take place while the RNA is denatured by heat and/or low salt conditions.

VI. RNA MODIFICATION

The electrophile can be added to the RNA to yield 2'-O-adducts at flexible nucleotide positions. The reaction can then be incubated until essentially all of the electrophile has either reacted with the RNA or has degraded due to hydrolysis with water. No specific quench step is required. Modification can take place in the presence of complex ligands and biomolecules as well as in the presence of a variety of salts. RNA may be modified within cells and viruses as well. These salts and complex ligands may include salts of magnesium, sodium, manganese, iron, and/or cobalt. Complex ligands may include but are not limited to proteins, lipids, other RNA molecules, DNA, or small organic molecules. The modified RNA can be purified from reaction products and buffer components that can be detrimental to the primer extension reaction by, for example, ethanol precipitation.

VII. PRIMER EXTENSION

Analysis of RNA adducts by primer extension in accordance with the presently disclosed subject matter can include in various embodiments the use of an optimized primer binding site, thermostable reverse transcriptase enzyme, low $MgCl_2$ concentration, elevated temperature, short extension times, and combinations of any of the forgoing. Intact, non-degraded RNA, free of reaction by-products and other small molecule contaminants can also be used as a template for reverse transcription. In some embodiments, 5'-radiolabeled DNA primers can be annealed to the RNA and extended to sites of modification in the presence of dNTPs by the activity of reverse transcriptase (RT). The RNA component of the resulting RNA-cDNA hybrids can be degraded by treatment with base. The cDNA fragments can then be resolved using, for example, a polyacrylamide sequencing gel, capillary electrophoresis or other separation technique as would be apparent to one of ordinary skill in the art after a review of the instant disclosure.

The deoxyribonucleotide triphosphates dATP, dCTP, dGTP, and dTTP can be added to the synthesis mixture, either separately or together with the primers, in adequate amounts and the resulting solution can be heated to about 90-100° C. from about 1 to 10 minutes. After the heating period, the solution can be cooled. In some embodiments, an appropriate agent for effecting the primer extension reaction can be added to the cooled mixture, and the reaction allowed to occur under conditions known in the art. In some embodiments, the agent for polymerization can be added together with the other reagents if heat stable. In some embodiments, the synthesis (or amplification) reaction can occur at room temperature. In some embodiments, the synthesis (or amplification) reaction can occur up to a temperature above which the agent for polymerization no longer functions. Thus, for example, if reverse transcriptase is used as the agent, the temperature can generally be no greater than about 60° C.

The agent for polymerization can be any compound or system that functions to accomplish the synthesis of primer extension products, including for example, enzymes. Suitable enzymes for this purpose include, but are not limited to, *E. coli* DNA polymerase I, Klenow fragment of *E. coli* DNA polymerase, polymerase muteins, reverse transcriptase, other enzymes, including heat-stable enzymes (i.e., those enzymes that perform primer extension after being subjected to temperatures sufficiently elevated to cause denaturation), such as murine or avian reverse transcriptase enzymes. Suitable enzymes can facilitate combination of the nucleotides in the proper manner to form the primer extension products that are complementary to each polymorphic locus nucleic acid strand. In some embodiments, synthesis can be initiated at the 5' end of each primer and proceed in the 3' direction, until synthesis terminates at the end of the template, by incorporation of a dideoxynucleotide triphosphate, or at a 2'-O-adduct, producing molecules of different lengths.

The newly synthesized strand and its complementary nucleic acid strand can form a double-stranded molecule under hybridizing conditions described herein and this hybrid is used in subsequent steps of the method. The newly synthesized double-stranded molecule can then be subjected to denaturing conditions using any of the procedures described above to provide single-stranded molecules.

VII. SEQUENCING

Sequencing lanes generated by dideoxy nucleotide incorporation can be used to assign bands in (+) and (−) electrophile samples. In some embodiments, one or two sequencing reactions can be sufficient to infer the entire sequence. In some embodiments, these steps can be performed concurrently with the primer extension reactions for the (+) and (−) electrophile samples.

Figure 2:
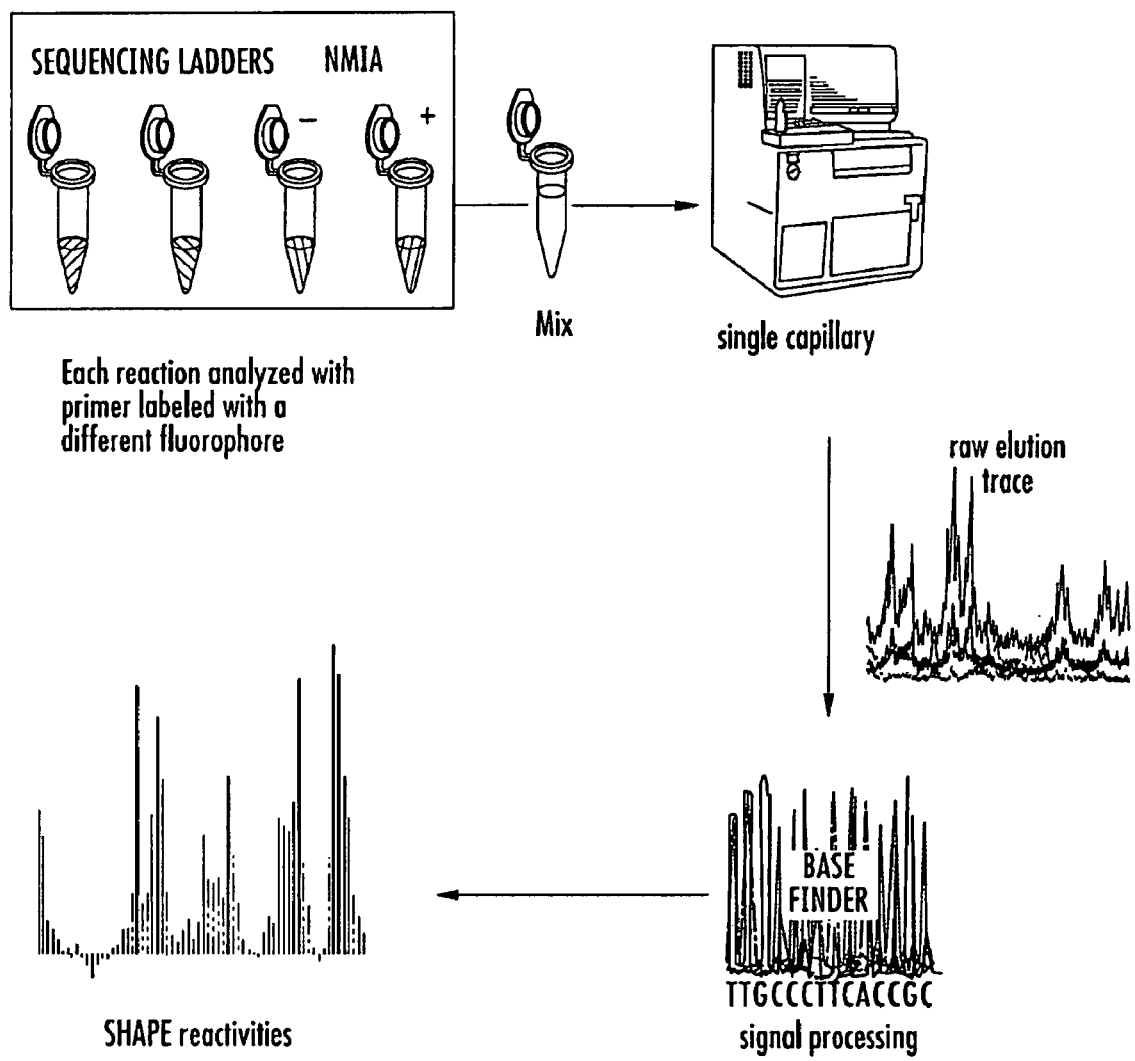
FIG. 2 is a schematic representation of the steps of an hSHAPE experiment. Sequencing ladders and (+) and (−) NMIA extensions are performed using different fluorophores but with the same primer sequence. The resulting cDNAs are separated on a DNA sequencer. Raw elution traces are analyzed by BaseFinder software as disclosed herein. An exemplary analyzed sequence (SEQ ID NO: 4) is shown. Correction for signal decay and normalization yield absolute SHAPE reactivity as a function of nucleotide position.

An hSHAPE experiment can comprise four different reactions: a (+) electrophile, a (−) electrophile control and two dideoxy sequencing reactions (FIG. 2). Each of these extension reactions can be performed using a 5'-fluorophore labeled DNA primer. In some embodiments, the reaction and extension conditions can be identical to a gel-based experiment, except that primer concentration is on the order of RNA concentration to ensure readable signal. The fluorophores employed by hSHAPE can be identical to the dyes normally used for DNA sequencing. The products of the extensions can be combined and purified by, for example, recovery with ethanol precipitation, and resolved in a single multi-fluor run by automated capillary electrophoresis.

IX. ANALYSIS OF hSHAPE DATA

IX.A. Processing Raw Elution Traces

In some embodiments, the resulting raw elution trace for the 5'-end of a target sequence can resemble a DNA sequencing experiment in that it can reflect the products of specific primer extension termination events. However, in an hSHAPE experiment, the absolute peak intensities as well as the elution times of peaks can be meaningful in the (+) and (−) electrophile traces. For example, missing peaks or peaks with low reactivity in the (+) electrophile trace correspond to RNA nucleotides constrained by base pairing or other interactions. Intense peaks in the (+) electrophile trace identify unstructured or flexible nucleotides, i.e., unconstrained nucleotides, in the RNA. In some embodiments, peak elution time and peak intensity indicates the sequence of reactive and unreactive nucleotides in an RNA.

Each hSHAPE experiment can contain a large peak at the low elution time that corresponds to unextended primers. A large peak corresponding to full length RNA can be observed at long elution times if the read extends to the 5'-end of an RNA. Between these two peaks, quantitative, single-nucleotide resolution RNA structure can be obtained.

The presently disclosed subject matter employs in some embodiments the signal processing framework of BaseFinder (Giddings et al. (1998) *Genome Res* 8:644-665) to analyze raw fluorescence versus elution time profiles. BaseFinder is a modular, extensible software package originally designed for DNA base calling and sequencing analysis. As discussed herein, the modified BaseFinder can function by applying a sequence of tools to a data trace. Each tool can perform an analysis step, and can contain adjustable parameters to account for experimental and stochastic variables, such as dye set and fluorescent baseline.

The initial processing steps of raw sequencer traces can be identical to those used for DNA sequencing. In some embodiments, fluorescent baseline can be subtracted for each channel. Next, color separation can be performed to correct for spectral overlap of the multiple dyes such that each channel reports quantitative cDNA amounts. In some embodiments, the final analysis step can be the alignment of corresponding peaks in the four channels because each fluorophore imparts a slightly different electrophoretic mobility on cDNAs of the same length. The result of these analysis steps can be an aligned plot of dye amount versus elution time for all the reactions in the SHAPE experiment. Each peak represents the amount of cDNA of a specific length. Corresponding peaks in all 4 traces can be aligned so that they have the same elution time.

In some embodiments, mobility shift and color separation parameters for a specific dye set can be generated by analysis of separate RNA sequencing experiments. To develop color separation parameters for each dye, spectral overlap in each channel can be determined in the absence of other fluorophores by analysis of a single nucleotide ladder. To develop mobility parameters, each of the different fluorophores can be used to generate the same nucleotide ladder from the same RNA template. In some embodiments, the ladders can be separated in the same capillary column. Mobility shifts can be determined by matching corresponding sequencing peaks throughout the read. Mobility and color separation parameters can be specific to a dye set, and can be used on multiple RNA reads.

IX.B. Quantification of Sequencer Data

Novel analysis steps can be employed in quantifying cDNA amounts in the (+) and (−) electrophile data traces to develop RNA structural constraints. Unlike DNA sequencing, where peak position is the most important factor, both the location and intensity of peaks in the electrophile data traces can be important to locate and quantify nucleotide flexibility.

The presently disclosed methods provide a BaseFinder tool, referred to herein as Align and Integrate, that calculates peak area in the (+) and (−) electrophile traces versus nucleotide sequence. First, Align and Integrate can detect and align peaks in the (+) and (−) electrophile traces with the RNA sequencing traces. Second, sequencing traces can be compared and aligned with the sequence of the RNA being studied. Align and Integrate can automatically account for the observation that cDNAs generated by sequencing are exactly 1 nucleotide longer than corresponding positions in the (+) and (−) electrophile traces. Finally, areas under each peak can be determined by performing a whole trace Gaussian-fit integration. The overall result of applying the presently disclosed programs to raw SHAPE traces is a set of (+) and (−) electrophile trace peak areas for every nucleotide position in the read.

Inspection of the resulting intensity data can indicate signal decay associated with the (+) electrophile trace. The signal reflects both the nature of electrophile reactivity as well as imperfect processivity of the reverse transcriptase enzyme. The drop can be corrected by assuming that the probability of extension at each nucleotide is constant and slightly less than one:

$$D = Ap^{(elution\ time)} + C,$$

where D is the signal decay adjustment factor, A and C are scaling factors that reflect the arbitrary initial and final intensities of the trace, and p is the probability of extension at each nucleotide. In some embodiments, typical values for p are about 0.995-0.999 for elution times in units of 2 measurements per second. The equation can be applied to peak intensities representing average reactive nucleotides throughout the trace. In some embodiments, the 2% of the most highly reactive peaks as well as peaks with reactivities near zero can be excluded from the calculation. Each peak intensity calculated at the same elution time is then divided by D. Signal decay correction can provide an unbiased data set that does not lose overall intensity as a function of readlength. Signal decay has also sometimes been observed in the sequencing lanes. Although uncommon, signal decay can also occur in the (−) electrophile trace if overall peak intensity is high in that trace. The steps to correct decay are the same as those for the (+) electrophile trace.

By way of additional example and not limitation, a statistical analysis can be performed to remove outliers from curve fitting. By way of further example, in the BaseFinder software package disclosed herein, a "Signal Decay Correction" feature provides a statistical analysis to determine outliers and removes outliers from the curve fitting.

Because the (+) and (−) electrophile extensions can be performed independently and use sequencing dyes with different quantum yields and spectral properties, the absolute scale for the (+) and (−) electrophile peak intensities are different. In order to quantitatively compare (+) and (−) electrophile peak intensities, it can be assumed that the peaks with the lowest about 10% of intensities throughout the (+) electrophile data accurately reflected the intensity of the corresponding (−) electrophile traces. All peak intensities in the (−) electrophile trace were multiplied by an appropriate factor that matched intensities to the unreactive nucleotides in the trace. The approach is insensitive to the dyes chosen for the (+) and (−) electrophile extensions. Indeed, interchanging the dyes used for the extensions produces nearly identical results.

Thus, also provided herein are methods for correcting signal decay for calculated peak intensities in an RNA structure analysis experiment. Signal decay is inherent to experiments that require primer extension. Peak intensity can decrease as a function of read length. A single exponential decay can used to correct for the signal decay, whose parameters are based on these assumptions. A representative equation is $y = ab^x + c$, where x is the trace elution time, and y is the correction factor for that time. a, b, and c can be changed to better fit the data of individual data sets. Each peak intensity in the (+) reagent data set can be divided by the value of the equation calculated at the elution time of the peak. The result is that specific peak intensities are equally probable regardless of nucleotide position. Normalized peak intensities can be accurately and quantitatively represented local nucleotide flexibility as a function of nucleotide position.

IX.C. hSHAPE Authentically Measures Local Nucleotide Flexibility

Highly reactive nucleotides have similar SHAPE reactivities, independent of whether they lie at the 5' or 3' end of the RNA. By way of non-limiting example, absolute SHAPE reactivities, superimposed on the well-characterized TAR and Poly(A) stem loops (nts 1-104) of the HIV-1 genome, show that SHAPE information is exactly consistent with the consensus secondary structure for this region. Nucleotides in loops are reactive whereas base paired nucleotides are unreactive. Notably, SHAPE reactivities also accurately report fine-scale structural differences. For example, nucleotides in the UCU bulge show intermediate reactivities, consistent with NMR studies that indicate that these nucleotides in the TAR stem are partially stacked. Reactive nucleotides are also referred to herein as "unconstrained" nucleotides.

Thus, also disclosed are methods for calculating absolute nucleotide 2'-OH reactivity, at single nucleotide resolution, by statistical analysis. Dyes used to generate (+) and (−)

reagent data have different quantum yields. Also, extension reactions are subject to random experimental error. The overall effect in some instances is that the intensities in the (+) and (−) reagent datasets are not quantitatively proportional to each other. Calculated peak intensities corresponding to each nucleotide in an RNA can be matched by assuming that low peaks intensities in the (+) reagent dataset are equivalent to corresponding peak intensities in the (−) reagent dataset. Matching can be achieved by multiplying the (−) reagent dataset by a factor. The factor can be determined manually by visual inspection of datasets. The factor can be calculated using statistical analysis. Once the intensities are matched, absolute reactivity at single nucleotide resolution can be calculated by subtracting the (−) reagent dataset from the (+) reagent dataset.

IX.D. hSHAPE on Long RNAs

A single hSHAPE experiment can efficiently interrogate structural constraints for RNA about 300-600 nucleotides long. For longer RNAs, it can be necessary to combine multiple overlapping reads of the RNA from separate primer sets. To combine structural constraints from multiple reads in a single data set, each read can be normalized to the same scale. Each SHAPE data set contains a few (about 2%) exceptionally reactive positions, which do not represent generically flexible nucleotides. The normalization factor for each data set can be determined by first excluding the most reactive 2% of peak intensities and the calculating the average for the next 8% of reactivities. All reactivities are then divided by this average.

The simple normalization procedure generates SHAPE reactivities on a scale, for example, from 0 to about 2, where 1.0 is the reactivity of a flexible nucleotide. Nucleotides with reactivities greater than about 0.8 are generally single stranded, while positions with reactivities less than about 0.2 are generally paired. Nucleotides with normalized SHAPE reactivities between 0.2 and 0.8 can be paired or can participate in other partially constraining interactions. The standard deviation at each nucleotide averages about 0.1 SHAPE unit, as determined by repeat and overlapping reads, for example, on the HIV-1 genomic RNA.

Also disclosed herein are methods for normalizing, comparing, and/or joining different data sets containing RNA structural information. Each data set can contain some nucleotides that exhibit hyper-reactivity, as well as a number of nucleotides that represent generic flexible positions. In some embodiments, the hyper-reactive nucleotides can be identified and excluded from normalization (usually 24% of the most highly reactive nucleotides). The reactivities of generically reactive nucleotides (usually the next 8-10% of nucleotides) are then averaged, and the values in the entire data set are normalized to this average. In some embodiments values are assigned. For example, a value of 1 can be used to represent an average flexible nucleotide and 0 can be used to represent a nucleotide of no reactivity with a reagent. In this case a value of 0.8 and above can be viewed as nearly always single stranded and values below 0.2 can be viewed as nearly always base paired. Joining ends of independent reads using different primer sets can be achieved accurately by careful adjustment of the signal decay correction parameters.

IX.E. Development of an RNA Structure from hSHAPE Constructs

SHAPE reactivities report direct and quantitative information regarding the extent of structure at each nucleotide in an RNA. An application of SHAPE technology is to develop well-supported structural models for a given RNA. The most successful structure prediction algorithms, such as for example RNAstructure (Mathews et al. (2004) *PNAS USA* 101:7287-7292), use a thermodynamic model based on nearest-neighbor free energy parameters to calculate the ΔG for potential structures for a given RNA sequence. The structure with the lowest calculated ΔG becomes the most highly predicted structure. However, the thermodynamic models used by these programs are approximate and RNA structure can be modulated by non-thermodynamic constraints. Therefore, in silico methods often predict different structural topologies with nearly identical energies for a given sequence. Without additional structural information, it is not possible to choose which predicted structure reflects the native conformation of an RNA sequence.

The presently disclosed methods facilitate structure prediction by including hSHAPE constraints in developing structural models. In some embodiments, an energetic penalty or credit can be applied for pairing each nucleotide according to their SHAPE reactivity. This "quasi-energetic" constraint provides a convenient and straightforward method for including SHAPE based constraints in structure prediction. In some embodiments, quasi-energetic constraints can be an approximation of energetic penalties associated with pairing a nucleotide of a specific absolute SHAPE reactivity. In some embodiments, the RNA structure program is modified to include these embodiments.

To incorporate the quantitative nature of hSHAPE constraints into structure prediction, the "quasi-energy" can be calculated by:

$$\Delta G_{SHAPE} = m \ln [\text{SHAPE reactivity} + 1.0] + b,$$

which can be applied to each nucleotide in each stack of two base pairs. Therefore, in some embodiments, the quasi-energy can be added twice per nucleotide paired in the interior of a helix and once per nucleotide paired at the end of a helix. The intercept, b, is the energy bonus for formation of a base pair with zero or low SHAPE reactivity while m, the slope, drives an increasing penalty for base pairing as the SHAPE reactivity increases. In one example, the b and m parameters shown to most likely produce a correct structure were −0.6 and 1.7 kcal/mol, respectively (per nucleotide). But these can be varied to modulate the energetic contribution of SHAPE reactivities in structure prediction.

Evidence from known RNA structures suggests that pairings between nucleotides 600 positions apart or more are nearly nonexistent, and 90% of base pairs occur between positions less than 300 nucleotides distant in sequence. Therefore, constraining maximum sequence distance between pairing partners can improve the predictive power of a structure-predicting program like RNAstructure. The presently disclosed methods incorporate in some embodiments a tool that completely forbids pairings between positions greater than an arbitrary distance apart in sequence. To develop structural models, using a maximum allowed distance between base pairs of 600 provides sufficient constraints for many RNAs. Reducing this value to about 300 can be helpful in locating short, poorly predicted, and transient pairings that can be explained by more probable shorter distance interactions.

To assess the robustness of a structural prediction, the thermodynamic penalty of pairing associated with hSHAPE reactivities can be varied. Predicted base pairs can be assigned a "pairing persistence" based on the range of parameters in which they are observed. Helices considered to be highly persistent can be observed even when the parameters in the above equation were set to values as high as b=0 and m>4. Increasing b and m has the effect of increasing the contribution of the SHAPE reactivity information on the secondary structure calculation. Helices with low pairing persistence are observed only at lower SHAPE-imposed penalties.

Varying the quasi-energetic contribution of SHAPE reactivity information in structure prediction can be useful in supporting a single secondary structure model when several are predicted at a single set of constraints. Predicted helices that exist under the most stringent parameters are most likely also exist under less stringent parameters. By incrementally decreasing the stringency of parameters, a structural model with high pairing persistence can be "built" with the assistance of SHAPE parameters.

Using hSHAPE and maximum pairing distance to constrain RNA secondary structure prediction has a dramatic impact on the quality of predicted structures. For example, prediction accuracy improves from 52% to 90% for the 154 nucleotide RNase P specificity domain and from 38% to 87% for the 1542 nucleotide *Escherichia coli* 16S rRNA. SHAPE-directed predictions characteristically include overall topologies that closely resemble the correct structure and errors tend to reflect small local structural rearrangements at the ends of helices and at multi-helix junctions.

Thus, also disclosed herein are methods for incorporating experimental structural constraints into RNA structure prediction programs. Nucleotide reactivities can be used to develop accurate RNA secondary structures. RNA structural constraints can be used as quasi-energetic constraints. In some embodiments a specific equation is employed:

$$\Delta G_{SHAPE} = m \ln[\text{normalized structural constraint} + 1.0] + b,$$

where m and b are user-definable. It can be assumed that structural elements that are predicted under the most stringent constraints and that persist as constraints are decreased become the most well-predicted elements of RNA structure. Changing the stringency of the constraints can also be used to identify the most highly defined topology when different structural topologies are predicted under a single set of constraints. Incorporation of maximum pairing distance constraints can be included to forbid highly unlikely RNA base pairings.

IX.F. hSHAPE Conclusions hSHAPE technology represents a significant improvement to the SHAPE approach. No longer limited by gel electrophoresis, structural reads as long as 600 nucleotides can be accomplished in about 8 hours. The increased read length of hSHAPE technology decreases the amount of effort necessary to analyze long RNAs. The steps of an hSHAPE experiment can be completed in parallel, making it theoretically possible to complete dozens of analyses in a single day.

Additionally, a set of steps has been developed to propose accurate, well-defined RNA secondary structures from raw sequencer data. These steps can be incorporated into computer algorithms, to enhance speed and other aspects of the analysis.

Several RNA molecules of interest are thousands of nucleotides long, including some mRNAs as well as viral genomes. hSHAPE allows analyzing the structure of and proposing structural models for such RNAs experimentally tractable. As an extreme example of RNA length, the SARS coronavirus RNA genome is 29,751 bases long. Assuming a readlength of 600 nucleotides and an overlap of 200 nucleotides at either end of the read, the entire SARS coronavirus can be interrogated, in duplicate, in less than 200 reads.

Also disclosed herein are methods for detecting efficient primer, protein, and small molecule binding sites using single nucleotide RNA structural information. The presently disclosed methods for RNA structure analysis can be used to identify long regions of flexible nucleotides. These regions can efficiently bind DNA or RNA primers. These regions of flexible nucleotides can represent efficient siRNA or antisense primer binding sites. Analysis of RNA structure in the presence and absence of protein or small molecule will indicate changes that can be interpreted as specific binding sites.

X. EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Reagents

All reagents as well as reaction tubes and equipment should be maintained free of RNase contamination. For best results, all chemicals should be purchased at the highest quality available and reserved for RNA use only.

5×SSIII FS Buffer 250 mM Tris (pH 8.3), 375 mM KCl, 15 mM $MgCl_2$

10×PNK buffer (New England Biolabs, Ipswich, Mass., United States of America)

0.5×TE 5 mM TRIS, pH 8.0, 0.5 mM EDTA

DNA Primer

Primers that are about 18-20 nt in length that form a 3' G-C base pair with the target RNA.

Acid Stop Mix

4:25 (v/v) mixture of 1 M unbuffered TRIS-HCl and Stop Dye

Stop Dye

85% formamide, ½×TBE, 50 mM EDTA, pH 8.0, containing bromophenol blue and xylene cyanol tracking dyes

γ-[$^{32}$P]-ATP

6×10$^6$ Ci/mol, 10 Ci/L, Perkin Elmer (Waltham, Mass., United States of America)

3.3×RNA Folding Mix 333 mM HEPES, pH 8.0, 20 mM $MgCl_2$, 333 mM NaCl. Other conditions that are known to stabilize the structure of the RNA under study can be used as well. Both buffering component and ionic strength can be varied. In the modification reaction, buffer concentration should be at least twice the NMIA concentration and adjusted to pH 8.

10×NMIA in DMSO

The concentration of this solution can vary with RNA length. For RNA reads of 100, 200 and 300 nucleotides, 10×NMIA concentrations of 130, 65 and 30 mM, can be used. Due to the solubility of the reagent, the stock concentration of NMIA is desirably not greater than 130 mM.

SHAPE Enzyme Mix 250 mM KCl, 167 mM TRIS HCl, pH 8.3, 1.67 mM each dNTP, 17 mM DTT, 10 mM $MgCl_2$.

5'-[$^{32}$P]-Labeled Primers

1 µL 60 µM DNA primer, 16 µL γ-[$^{32}$P]-ATP, 2 µL 10×PNK buffer, and 1 µL T4 Polynucleotide Kinase were mixed well. Incubate at 37° C. for 30 min. Purify on 20% denaturing polyacrylamide gel (1×TBE, 7 M urea). Use autoradiography to visualize and excise the band corresponding to the radiolabeled DNA primer. Passive elute overnight into water and remove small pieces of acrylamide from the RNA using a centrifugal filter device. Recover radiolabeled DNA by ethanol precipitation. Dissolve the pellet in 100 μL 1 mM HEPES, pH 8.0. The final primer solution concentration is about 0.3 μM.

Example 1

Selective 2'-Hydroxyl Acylation Analyzed by Primer Extension (SHAPE)

Quantitative RNA Structure Analysis at Single Nucleotide Resolution RNA Folding

Two (2) pmol RNA was added in 12 μL 0.5×TE buffer to a 200 μL thin-walled PCR tube. The RNA was heated to 95° C. for 2 minutes and immediately placed on ice for 2 minutes. Six (6) μL folding mix was added and the solutions were mixed by gentle repetitive pipetting. The tube was then removed from the ice and incubated at the desired reaction temperature for 20 minutes in a programmable incubator. While the tube was incubating, nine (9) μL of solution was removed and placed in a second tube. One tube was used for the (+) NMIA reaction, and the other tube was used for the (−) NMIA reaction.

RNA Modification

One (1) μL NMIA in DMSO was added to the (+) NMIA tube and 1 μL neat DMSO was added to the (−) NMIA tube. The tubes were then mixed well. The reaction was incubated for 5 NMIA hydrolysis half-lives. To estimate the NMIA half-life between 15° C. and 75° C., the following equation was used:

$$\text{half life(minutes)} = 360 \times \exp[-0.102 \times \text{temperature}(° C.)].$$

At 37° C., NMIA has a half-life of 8.3 minutes. Thus, at 37° C., the reaction was incubated for about 45 minutes.

After the reaction has gone to completion, the reactions were transferred to 1.5 mL centrifuge tubes and the modified RNA was recovered by ethanol precipitation. For the ethanol precipitation, 90 μL water, 4 μL 5M NaCl and 350 μL absolute ethanol were added to the tubes, the tubes were incubated at −80° C. for 30 minutes, and the RNA was sedimented by spinning at a maximum speed in a microfuge at 4° C. for 30 minutes.

After the ethanol supernatant was removed, the RNA was redissolved in 10 μL 0.5×TE buffer and the samples transferred to 200 μL thin-walled PCR tubes.

Primer Extension and RNA Sequencing

Three (3) μL radiolabeled primer solution was added to the (+) and (−) NMIA tubes. The tubes were then mixed by repetitive pipetting. To sequence the RNA for assigning bands in the (+) and (−) NMIA samples, 3 μL of primer solution was added to 1 pmol of RNA in 8 μL of 0.5×TE buffer. The primer was annealed to the RNA by incubating the tubes at 65° C. for 5 minutes and then at 35° C. for 20 minutes.

6 μL of SHAPE enzyme mix was added to the (+) and (−) NMIA reactions. 1-2 μL of one ddNTP solution was then added to each sequencing experiment. The tubes were heated to 52° C. for 1 minute. 1 μL of SUPERSCRIPT III™ was added to each tube. The tubes were mixed well by gentle repetitive pipetting. The tubes were immediately returned to the heat block and incubated at 52° C. for 10 minutes.

1 μL NaOH was added to the tubes to degrade the RNA. The samples were heated to 95° C. for 5 minutes. 29 μL of acid stop mix was added to the tubes and the tubes were incubated at 95° C. for 5 minutes.

cDNA Fragment Analysis by Gel Electrophoresis (+) NMIA, (−) NMIA, and sequencing reactions were loaded in individual lanes of a polyacrylamide sequencing gel (29:1 acrylamide:bis acrylamide, 1×TBE, 7 M urea). About 2 μL per lane was loaded. For extensions of 100 or fewer nucleotides, electrophoresis was performed for 150 minutes at 70 W. To visualize RNA extension reactions spanning more than 100 nucleotides, samples were reloaded after 150 minutes in unoccupied lanes on the gel and electrophoresis continued for an additional 150 minutes at 70 W. The sample loaded first will have been subjected to electrophoresis for about 300 minutes, yielding well-resolved positions near the 5' end of the RNA.

The gel was exposed overnight to a phosphor screen and scanned bands quantified using a phosphorimaging instrument. The intensity of every well-defined band in the gel for the (+) and (−) NMIA lanes was quantified by two-dimensional densitometry. This step was performed using the SAFA (Semi-Automated Footprinting Analysis) program.

Absolute NMIA reactivity at each position in the RNA was calculated by subtracting (−) NMIA intensities from (+) NMIA intensities. (+) and (−) NMIA intensities were normalized to each other by assuming the low intensity (unreactive) positions in each experiment have the same value. The calculation is equivalent to assuming that at least a few nucleotides will be unreactive in most RNAs. In assigning the SHAPE band positions, the cDNA markers generated by dideoxy sequencing were exactly 1 nucleotide longer than the corresponding (+) and (−) NMIA cDNAs.

SHAPE Results

Figure 3A:
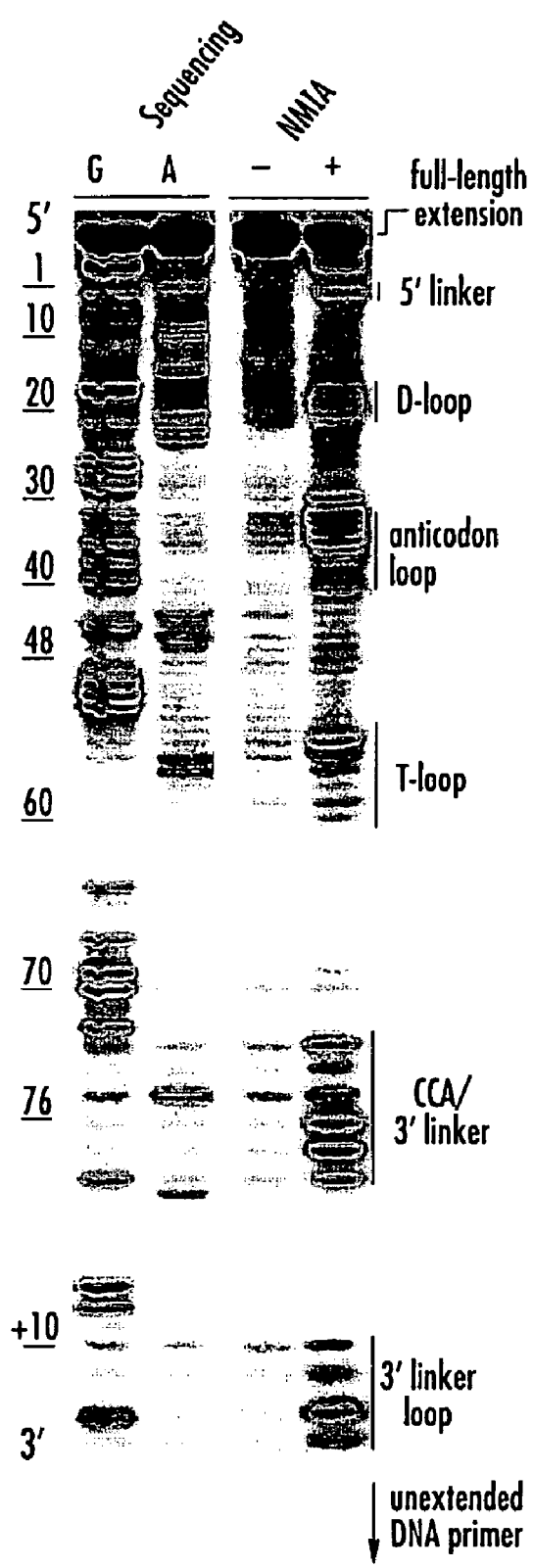
FIG. 3a is an autoradiograph of a sequencing gel illustrating a minimal SHAPE experiment.

A minimal SHAPE experiment consists of three or four lanes resolved in a sequencing gel (FIG. 3a). The representative experiment was performed using an in vitro transcript corresponding to yeast tRNA$^{Asp}$ embedded within a structure cassette. Two sequencing lanes were used to assign the SHAPE reactivities observed in the (−) and (+) NMIA reagent lanes. The bright bands at the top of the gel correspond to the relatively abundant full-length extension product. Bands corresponding to the unextended DNA primer and to short extension products, caused by pausing of reverse transcriptase during initiation of primer extension, were too short to be observed in the gel image. Approximately 90 RNA nucleotides were sufficiently well resolved such that absolute SHAPE reactivities were quantified.

Positions in which SHAPE reactivity was significantly higher in the (+) NMIA reaction as compared to the no reagent (−) control were emphasized with vertical bars and correspond precisely to hairpin loops and unconstrained linker regions in the tRNA$^{Asp}$ construct. Band intensities were quantified (FIG. 3b) and absolute SHAPE reactivities at almost every position within the RNA obtained by subtracting the (−) control intensities from the (+) NMIA intensities (FIG. 3c). Superposition of absolute band intensities on a secondary structure model for the tRNA$^{Asp}$ construct yielded very precise information regarding the pattern of base pairing and the formation of noncanonical tertiary interactions in the RNA (FIG. 3d).

Figure 4:
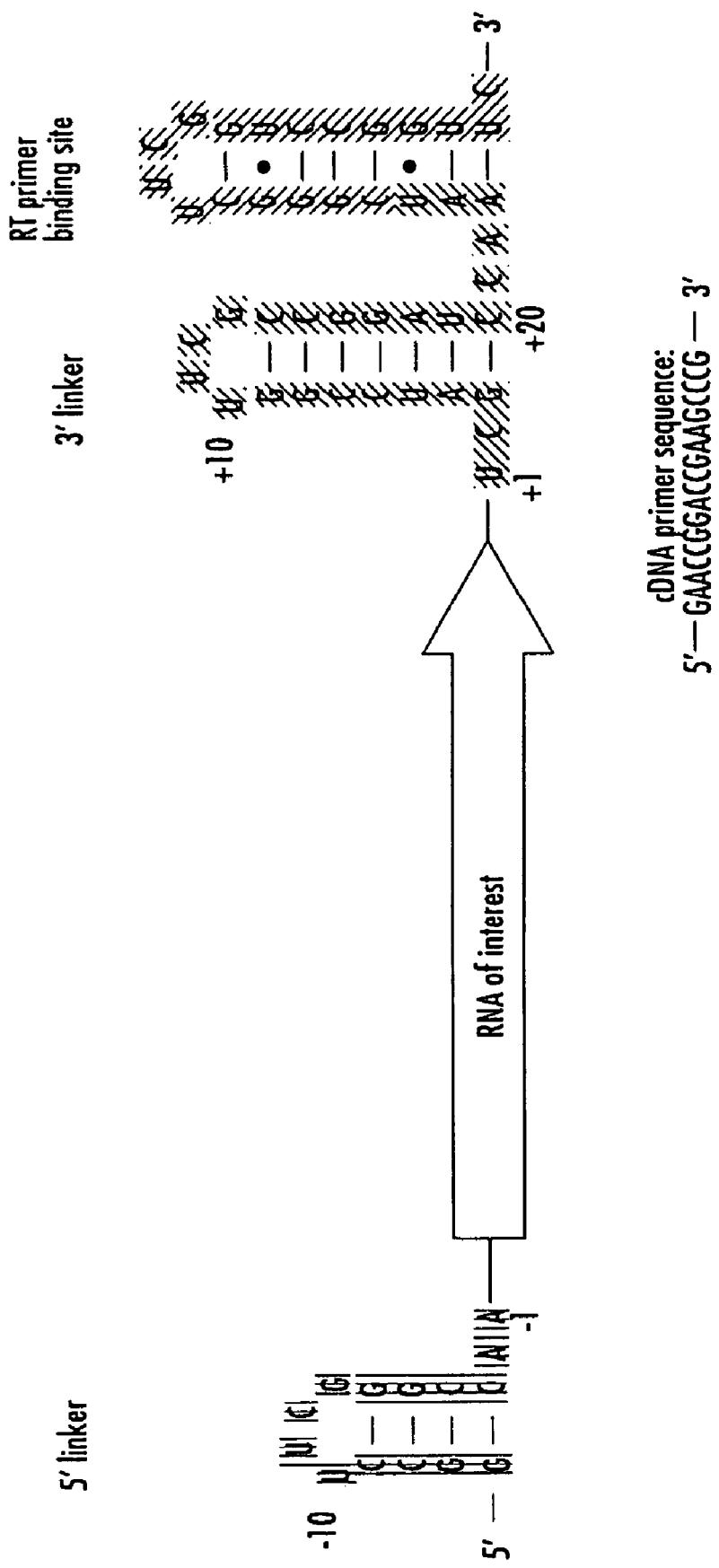
FIG. 4 is a schematic diagram presenting a structure cassette that contains 5' and 3' flanking sequences of 14 and 43 nucleotides (SEQ ID NO: 6 and SEQ ID NO: 7, respectively) and allows all positions within the RNA of interest to be evaluated in a sequencing gel. The cDNA primer sequence (SEQ ID NO: 3) is also shown in the lower right.

Almost all base paired positions in tRNA$^{Asp}$ were determined to be unreactive, whereas nucleotides in the T-, D- and anticodon loops were determined to be reactive. 5' and 3' flanking nucleotides have reactivities consistent with the design of the structure cassette (FIG. 4). SHAPE chemistry also correctly reported that most positions involved in tertiary interactions have low local nucleotide flexibility. For example, nucleotides in the linking loops (residues U8-A9 and G45-C50) that form idiosyncratic tertiary interactions with the D-stem are uniformly unreactive.

One important application of this technology is that SHAPE reactivities can be used to constrain the output of secondary structure prediction algorithms. For RNAs that do not contain pseudoknots, the RNAstructure program can be used to obtain well-defined and experimentally-constrained secondary structure models. Heuristically, nucleotides whose reactivities are at least 50% of the most reactive positions are typically single-stranded; whereas, nucleotides with reactivities that are 25-50% of this maximum reactivity are typically either single-stranded or adjacent to a single-stranded, bulged or mismatched nucleotide (this class of reactivity is implemented as the Chemical Modification constraint in RNAstructure). SHAPE information can then be sufficient to determine or strongly constrain possible secondary structure models for RNAs.

Example 2

A Fast Acting Reagent for Analysis of RNA Secondary and Tertiary Structure by SHAPE Chemistry Synthesis of [$^{32}$P]-Labeled pAp-Ethyl Adenosine-3'-(O-ethyl)-phosphate precursor (10 µM final) was 5'-[$^{32}$P]-labeled using T4 polynucleotide kinase (10 µL; containing 70 mM Tris-HCl, 10 mM MgCl$_2$, 5 mM dithiothreitol, 1 µL T4 PNK (10,000 units/mL), 60 µCi [γ-$^{32}$P) ATP; 37° C. for 1 hour) and purified by gel electrophoresis (30% polyacrylamide, 29:1 acrylamide:bisacrylamide, 0.4 mm×28.5 cm×23 cm; 30 W; 1 hour), excised from the gel, passively eluted into 300 µL HE (10 mM Hepes, pH 8.0, 1 mM EDTA; overnight at 4° C.); and separated from solid acrylamide by microfiltration.

Synthesis of 1-methyl-7-Nitroisatoic Anhydride (1M7)

To a suspension of 0.1656 g (4.14 mmoles) of sodium hydride (60% in mineral oil) in 20 mL DMF was added a solution of 0.6584 g (3.16 mmoles) of 4-nitroisatoic anhydride in 20 mL DMF. After stirring a few minutes at room temperature, a clear orange solution formed. 0.2615 g (3.2 mmoles) of methyl iodide was added to the reaction, and the mixture was stirred at room temperature for 4 hours. The reaction was poured into 50 mL of cold 1 N HCl, and the resulting bright orange precipitate was filtered and washed sequentially with water and ether to give 608.3 mg (86%) of product. $^1$H NMR (CO(CD$_3$)$_2$, 400 MHz,) δ 3.69 (s, 3H, —NCH$_3$—), 8.12 (dd, J=8.8 Hz, 2 Hz, 1H, ArH), 8.2 (d, J=2 Hz, 1H, ArH), 8.34 (d, J=8.4 Hz, 1H, ArH).

NMIA and 1M7 Hydrolysis and 2'-O-Adduct Formation

Hydrolysis was followed by adding (1.5 mM NMIA or 2.0 mM 1M7 in 300 µL DMSO) reagent to 1.1× buffer (2.7 mL, 6.7 mM MgCl$_2$, 111 mM NaCl, 111 mM HEPES (pH 8.0)) equilibrated at 37° C. in a cuvette. Pseudo-first-order rates were obtained by monitoring the absorbance of the hydrolysis product (at 360 nm for 2-methylaminobenzoate and 430 nm for 2-methylamino-4-nitrobenzoate). Rates of adduct formation for [$^{32}$P]-labeled pAp-ethyl (10,000 cpm/µL) were obtained by adding 10% (v/v) reagent (5 mM final NMIA or 1M7 in DMSO) to 1.1× reaction buffer, quenching the reaction with 1 vol 250 mM dithiothreitol, resolving by gel electrophoresis (30% polyacrylamide; 29:1 acrylamide:bisacrylamide; 0.4 mm×28.5 cm×23 cm; 30 W; 45 minutes), and quantifying by phosphorimaging. Reaction rates were obtained using an equation that accounts for parallel reaction of NMIA or 1M7 by 2'-O-adduct formation ($k_{adduct}$) and by hydrolysis ($k_{hydrolysis}$):

fraction product=
1−exp[($k_{adduct}$[reagent]/$k_{hydrolysis}$)($e^{-(k_{hydrolysis})t}$−1)].

Synthesis of *Bacillus subtilis* RNase P RNA

A DNA template for transcription of the specificity domain of the *B. subtilis* RNase P, inserted in the context of a 5' and 3' flanking structure cassette (see FIG. 4), was generated by PCR (1 mL; containing 20 mM Tris (pH 8.4), 50 mM KCl, 2.5 mM MgCl$_2$, 200 µM each dNTP, 500 nM each forward and reverse primer, 5 pM template, and 0.025 units/µL Taq polymerase; denaturation at 94° C., 45 seconds; annealing 55° C., 30 seconds; and elongation 72° C., 1 minutes; 38 cycles). The PCR product was recovered by ethanol precipitation and resuspended in 150 µL of TE (10 mM Tris (pH 8.0), 1 mM EDTA). Transcription reactions (1.5 mL, 37° C., 4 hours) contained 40 mM Tris (pH 8.0), 10 mM MgCl$_2$, 10 mM DTT, 2 mM spermidine, 0.01% (v/v) Triton X-100, 4% (w/v) poly (ethylene)glycol 8000, 2 mM each NTP, 50 µL of PCR-generated template, and 0.1 mg/mL of T7 RNA polymerase. The RNA product was purified by denaturing polyacrylamide gel electrophoresis (8% polyacrylamide, 7 M urea, 29:1 acrylamide:bisacrylamide, 32 W, 2 hours), excised from the gel, and recovered by electroelution and ethanol precipitation. The purified RNA (about 4 nmol) was resuspended in 100 µL TE.

Structure-Selective RNA Modification

RNA (2 pmol) in 5 µL ½×TE was heated at 95° C. for 2 minutes, cooled on ice, treated with 3 µL of 3× folding buffer (333 mM NaCl, 333 mM Hepes (pH 8.0), 33.3 mM MgCl$_2$ (or no MgCl$_2$)), and incubated at 37° C. for 20 minutes. The RNA solution was treated with 1M7 or NMIA (1 µL, 65 mM in anhydrous DMSO), allowed to react for 70 seconds (equal to five 1M7 hydrolysis half-lives, accompanied by a calorimetric change from pale yellow-orange to deep orange-brown upon completion) or 25 minutes (five NMIA hydrolysis half-lives). No-reagent control reactions contained 1 µL DMSO. Modified RNA was recovered by ethanol precipitation (90 µL sterile H$_2$O, 5 µL NaCl (5 M), 1 µL glycogen (20 mg/mL), 400 µL ethanol; 30 minutes at −80° C.) and resuspended in 10 µL of TE.

Primer Extension

A fluorescently labeled DNA primer (5'-Cy5 or Cy5.5-labelled GAA CCG GAC CGA AGC CCG (SEQ ID NO:3); 3 µL, 0.4 µM) was added to the RNA (10 µL, from the previous step) by heating to 65° C. (6 minutes) and 35° C. (20 minutes). Reverse transcription buffer (6 µL; 167 mM Tris (pH 8.3), 250 mM KCl, 10 mM MgCl$_2$, 1.67 mM each dNTP) was added; the RNA was heated to 52° C.; SUPERSCRIPT III™ reverse transcriptase (1 µL, 200 units) was added and reactions were incubated at 52° C. for 30 minutes. Primer extension reactions were quenched by addition of 4 µL of an equal mixture of EDTA (100 mM) and sodium acetate (3 M, pH 5.2). The resulting cDNAs were recovered by ethanol precipitation, washed twice with 70% ethanol, dried in a SPEEDVAC™ rotating evaporator for 10 min, and resuspended in 40 µL de-ionized formamide. Dideoxy sequencing markers were generated using unmodified RNA and primers labeled with unique fluorophores (D2 or IR800, I µM), and by adding 1 µL of 3'-deoxythymidine (10 mM) or 2',3'-dideoxyadenosine (2 mM) triphosphate after addition of reverse transcription buffer. The cDNA extension products were separated by capillary electrophoresis using a Beckman Coulter CEQ 2000XL DNA Analysis System.

Data Analysis

Raw traces from the CEQ 2000XL were processed in accordance with the presently disclosed subject matter software package. Reactivities for comparison of the (+) Mg$^{2+}$ and (−) Mg$^{2+}$ experiments were normalized to intensities at positions 101 and 102; all negative intensities were set to zero. The percent reactivity for each nucleotide was obtained by averaging the highest reactivities, corresponding to positions 123 and 196 for the (+) $Mg^{2+}$ and (−) $Mg^{2+}$ traces, respectively, and dividing all intensities by this average reactive value. On this scale, SHAPE reactivities were reproducible to ±5%. For the purpose of defining constraints for the RNA structure software program in accordance with the presently disclosed subject matter, the intensities for the (+) $Mg^{2+}$ experiment were normalized by excluding the top 2% of reactive nucleotides (3 nts), averaging the next 8% of reactive nucleotides (12 nts), and then dividing all intensities by this average high value to give intensities from 0 to slightly greater than 2. In the RNA structure, nucleotides with reactivities greater than 0.75 were required to be single stranded and positions with reactivities greater than 0.35 were prohibited from forming internal Watson-Crick pairs.

NMIA and 1M7 Analysis

Figure 5:
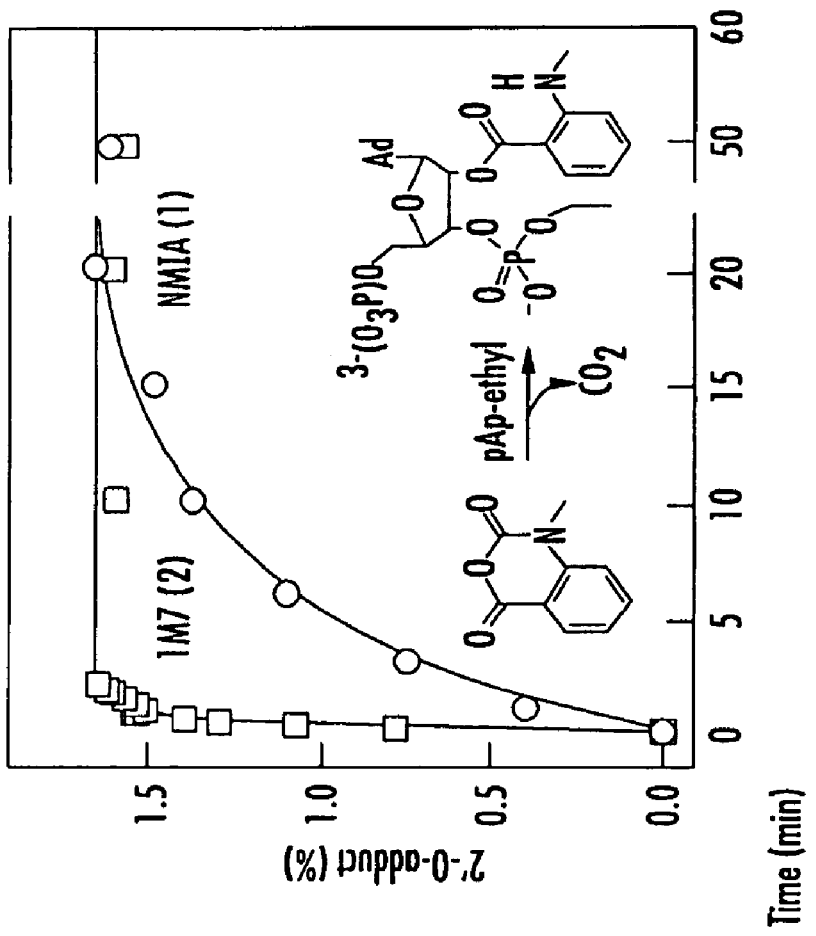
FIG. 5 is a graphical representation of the comparative reactivity of 1M7 and MNIA via hydrolysis (left panel) and 2'-O-adduct formation with pAp-ethyl (right panel).
Figure 5:
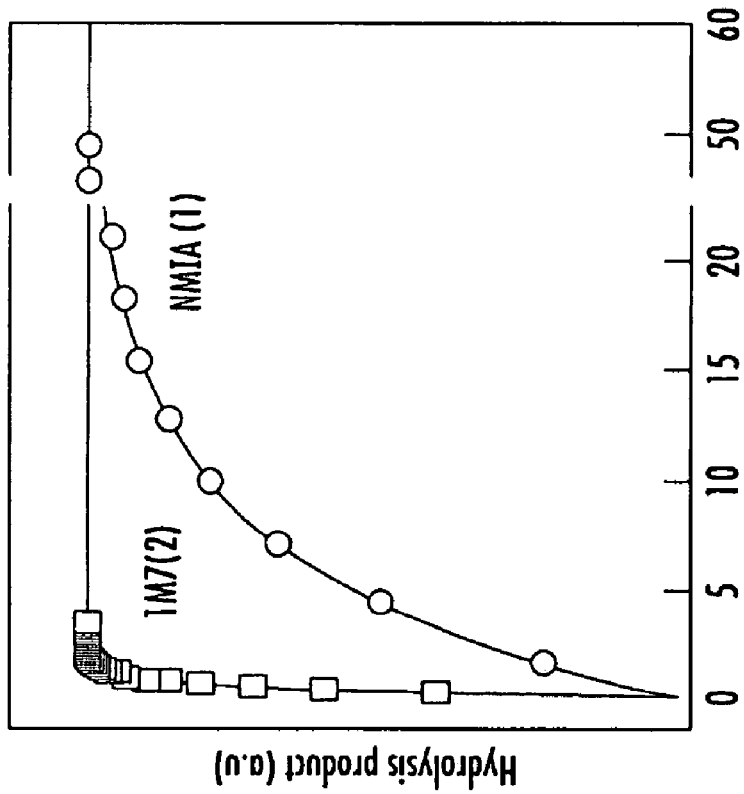

The reagent hydrolysis was monitored as the increase in UV absorbance of the aminobenzoate products. 1M7 was significantly more labile towards hydrolysis than NMIA. 1M7 undergoes hydrolysis with a half-life of 14 seconds and therefore the reaction is complete in about 70 seconds. In contrast, NMIA required over 20 minutes to react to completion (FIG. 5).

The ability of each compound to react with 3'-phosphoethyl-5'-adenosine monophosphate (pAp-ethyl) was then evaluated. pAp-ethyl contains a 2'-hydroxyl and 3'-phosphodiester monoanion. 1M7 reacted significantly more rapidly with pAp-ethyl than did NMIA. However, the final extent of 2'-O-adduct formation for the two compounds was identical, within error.

Identical extents of reaction for NMIA and 1M7, despite the much faster reactivity of 1M7, indicated that the rates of hydrolysis and of 2'-hydroxyl acylation increased by precisely the same 20-fold increment. The experiments indicated that 1M7 has the ideal chemical characteristics for a fast acting and self-quenching reagent for RNA SHAPE chemistry.

The extent to which 1M7 provides accurate and quantitative information regarding RNA structure using the specificity domain of the *Bacillus subtilis* RNase P enzyme was then evaluated. The specificity domain of the *Bacillus subtilis* RNase P enzyme was chosen because it is a large (154 nt) RNA with a known structure. The RNA spans numerous typical base-pairing and stacking interactions, a tetraloop-receptor tertiary interaction (involving L12 and P10.1) common to many large RNAs, and two large internal loops (J11/12 and J12/11) stabilized by an extensive series of non-canonical interactions.

A SHAPE experiment was performed on the RNase P domain under conditions that stabilize the native tertiary fold (6 mM $MgCl_2$, 100 mM NaCl, pH 8.0) by treating the RNA with 6.5 mM 1M7. Sites of 2'-O-adduct formation were identified as stops to primer extension, using fluorescently labeled DNA primers, resolved by capillary electrophoresis. Absolute SHAPE reactivities were calculated by subtracting the background observed in no-reagent control experiments that omitted 1M7. Reactivity at each nucleotide was classified as high, medium, low, or near-zero.

Superposition of the quantitative reactivity information on a secondary structure diagram for the RNase P specificity domain shows that a 70 second reaction with 1M7 accurately reports the known secondary and tertiary structure for the RNA. Essentially all nucleotides involved in Watson-Crick base-pairs were unreactive. Moreover, many non-canonical, but stable, U•G, A•A, and A•G pairs were unreactive. Nucleotides in P10.1 and in L12 that form the tetraloop-receptor tertiary structure motif were also unreactive.

In contrast, nucleotides in loops or adjacent to bulges or other irregularities were reactive. Nucleotides in the structurally idiosyncratic module involving J11/12 and J12/11 show a wide range of reactivities. Strikingly, the most highly conserved nucleotides in this module (A187, A191, G219-G220, A222), that participate in stabilizing tertiary interactions, also showed the lowest SHAPE reactivities using 1M7.

Figure 6:
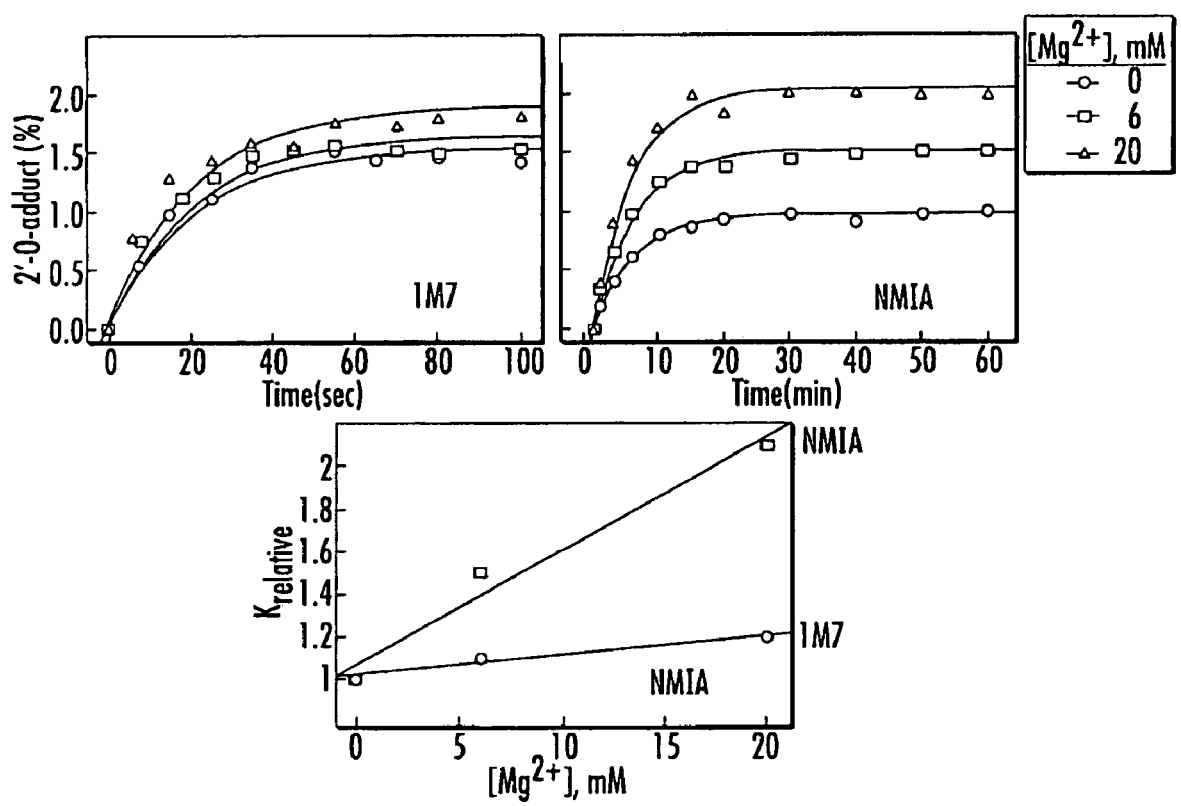
FIG. 6 is a series of graphs illustrating that the reaction between pAp-ethyl and 1M7 is independent of $Mg^{+2}$ concentration over the range 0-20 mM, whereas the reaction of pAp-ethyl with NMIA is not. The dependence of reaction rate on $Mg^{+2}$ concentration is indicated by both absolute rate and the extent of 2'-O-adduct formation at long time points for 0, 6, and 20 mM $Mg^{+2}$ (top). The change in rate from 0 to 20 mM $Mg^{+2}$ for 1M7 is negligible, while for NMIA the change is greater than 2-fold (bottom).

A similar SHAPE experiment in the absence of magnesium ion was conducted. Control experiments indicated that both reaction with the model nucleotide, pAp-ethyl, and 1M7 hydrolysis were independent of $Mg^{2+}$ concentration. This $Mg^{2+}$-independence represents an additional significant improvement over the parent compound, NMIA, whose reactivity is strongly dependent on ionic strength (FIG. 6). Thus, observed changes in SHAPE reactivity with 1M7 reflected changes in RNA secondary and tertiary structure and not $Mg^{2+}$-induced differences in reagent properties.

Figures 9A, 9B:
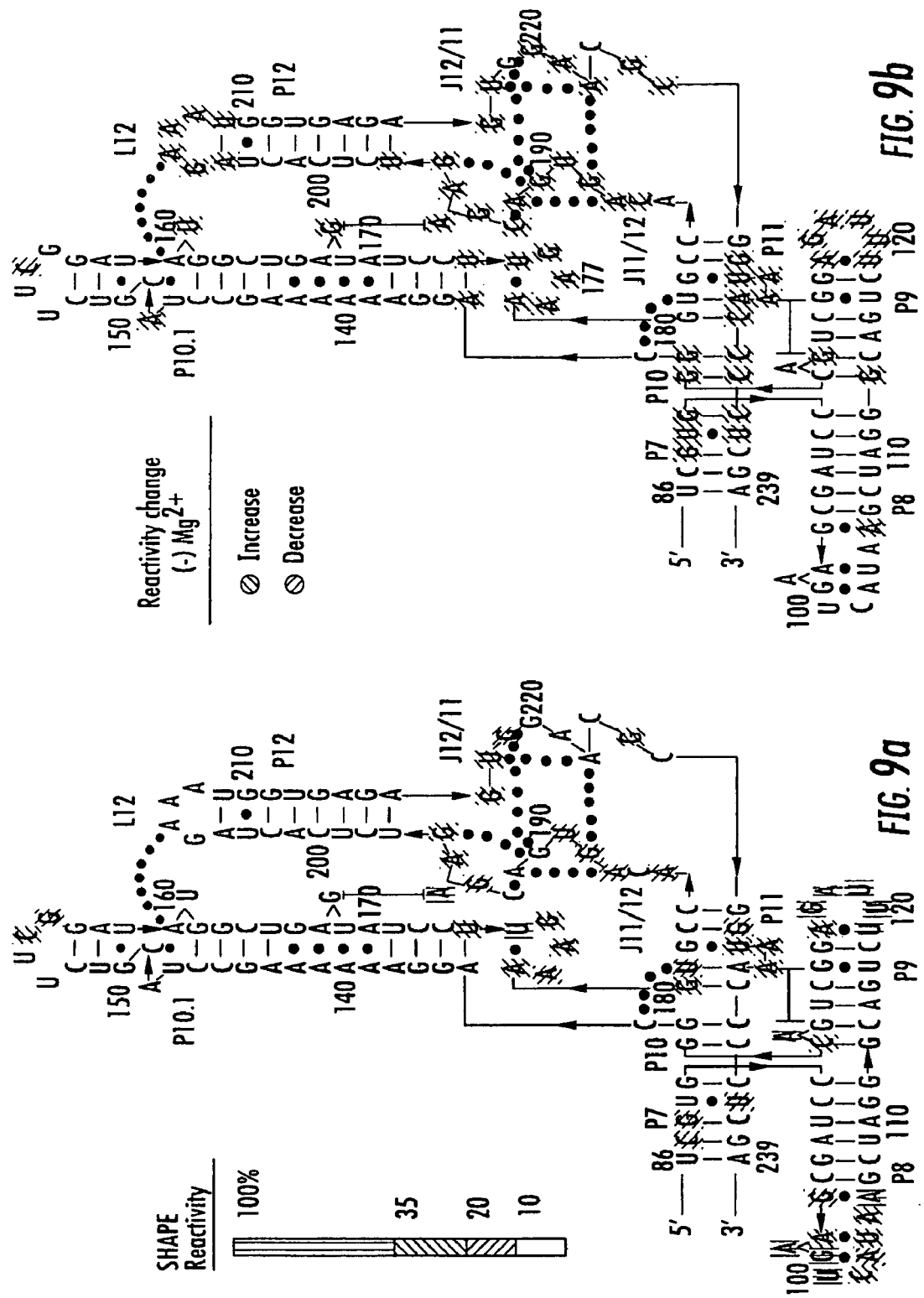
FIGS. 9a and 9b are schematic representations of base pairing and tertiary interactions for the specificity domain of *Bacillus subtilis* RNase P (SEQ ID NO: 10).

The effect of $Mg^{2+}$ on the structure of the RNA was quantified using a difference plot in which nucleotide reactivities in the (+) $Mg^{2+}$ experiment were subtracted from the (−) $Mg^{2+}$ experiment. Positive and negative peaks indicated an increase or decrease in local nucleotide flexibility in the absence of $Mg^{2+}$, respectively. Many sites in the (−) $Mg^{2+}$ experiment showed increased SHAPE reactivity. Increased reactivity occurred precisely at nucleotides that participated in tertiary interactions in the RNase P domain. SHAPE reactivity also showed that the irregularly stacked P7-P10-P11 helical domain unfolds when $Mg^{2+}$ is removed. See FIGS. 9$a$ and 9$b$.

The extent to which SHAPE information can be used to constrain the output of an RNA secondary structure prediction algorithm was then evaluated. Prediction accuracies were predicted both using the native secondary structure as the target and using a modified structure that excluded the $Mg^{2+}$-dependent base pairs in the P7-P10-P11 domain. When the specificity domain of *Bacillus subtilis* RNase P was folded in RNAstructure, the lowest free energy structure contained 52% of the correct pairs and features an overall topology that was radically different from the correct structure. When SHAPE reactivity information was added to constrain single-stranded and non-internal base pairs, the lowest free energy structure was 76% correct using the native secondary structure as the target and 91% correct when base pairs in the P7-10-P11 domain (which do not form in the absence of native tertiary interactions) were excluded. Using either target structure, the SHAPE-constrained prediction features an overall topology that closely resembled the correct structure.

SHAPE chemistry performed with 1M7 accurately reported the known structure of the RNase P specificity domain under native conditions. 1M7 reactivity detected nucleotides constrained both by base pairing and by idiosyncratic, non-canonical tertiary interactions. SHAPE chemistry enabled very precise analysis of the differences between two structures, such as $Mg^{2+}$-dependent tertiary interactions. 1M7 was easily handled in the laboratory and enabled analysis of large RNA structures at single nucleotide resolution in less than 70 seconds.

Example 3 hSHAPE Chemistry on the 5'-Most 300 Nucleotides of an HIV-1 Structural Model of the HIV-1 Genome To detect virion-specific RNA conformational changes and RNA-protein interactions, hSHAPE was used to analyze the structures of four states in total. In addition to (i) genomic RNA inside infectious virions (the in virio state), (ii) authentic HIV-1 RNA gently deproteinized and extracted from virions (ex virio), (iii) genomic RNA in which select RNA-protein interactions were disrupted by treatment with Aldrithiol-2 (AT-2 treated, described in detail below), and (iv) a 976-nucleotide HIV-1 monomer generated by in vitro transcription (termed the monomer state) were analyzed. Structural information for 94% of all nucleotides in these four states was obtained, with two-fold coverage or higher, for a total analysis of over 8,200 nucleotides.

SHAPE reactivities reported direct and quantitative information regarding the extent of structure at each nucleotide in an RNA. A combination of a thermodynamic model based on nearest-neighbor free energy parameters was then used in concert with quasi-energetic constraints, calculated from experimental SHAPE reactivities, to develop secondary structure models for HIV-1 genomic RNA.

The protein-free ex virio RNA was taken as the reference state for the secondary structure of the 5' end of the HIV-1 genome. The structure strongly reflects the constraints imposed by SHAPE reactivities. The well-determinedness of each helix in the secondary structure was assessed by varying the thermodynamic penalty imposed by the SHAPE constraints, termed the "pairing persistence". The most persistent helices were predicted even when SHAPE constraints were used to impose large pairing penalties for even slightly reactive nucleotides. Less persistent helices formed only at a lower SHAPE-imposed pairing persistence.

Given the similarities in the primary reactivity data for SHAPE and for prior analyses using conventional reagents, elements of the SHAPE-constrained secondary structure were determined to be similar to previously proposed models (Damgaard et al. (2004) *J Mol Biol* 1336:369-379; Paillart et al. (2004) *J Biol Chem* 279:48397-48403; Berkhout et al. (2002) *J Biol Chem* 277:19967-19975). For example, there is a strong consensus regarding the structures of several stem-loop motifs including the TAR, Poly(A), DIS, SD, and T elements. SHAPE analysis also supports formation of a previously proposed long-range pseudoknot (nts 79-85/443-449) (Paillart et al. (2002) *J Biol Chem* 277:5995-6004.

The secondary structure model also contained substantive differences with respect to previous models, reflecting several factors unique to the presently disclosed approach. First, the hSHAPE data set was 94% complete. In the case of HIV-1 genomic RNA, relatively little data had been obtained for positions 110-125, 236-243, 276-282, 408-415, 432-435, and 465-477 and no data was available 3' of position 720, which led to structural proposals that were not consistent with the more complete hSHAPE data set. Second, end effects dramatically altered structure prediction when only small pieces of a large RNA were analyzed. Structures that involve or lie inside of long-range interactions, such as the 108-114/335-341 stem mispredicted if the RNA sequence does not include the complete domain. Third, incorporation of SHAPE reactivity information as a pseudo-energy term makes the structure prediction calculation insensitive to errors in any single reactivity measurement.

Structural Differences in Regulatory Versus Coding Regions

The 5' end of the HIV genome spans two functional regions whose boundary lies at the AUG start codon for the Gag coding sequence (nts 336-338). Positions upstream of the AUG codon comprise a 343 nucleotide long 5' regulatory domain, whereas nucleotides 3' of the start codon span the Gag coding region, of which 560 nucleotides were mapped. It is currently not possible to distinguish coding versus non-coding regions by secondary structure prediction alone.

By two criteria, SHAPE reactivities indicated that the 5' regulatory domain was more highly structured than the 3' mRNA-like region. First, the average SHAPE reactivity, a metric for the extent of structure in the two regions, is 0.30 for the 5' regulatory domain and 0.44 for the 3' mRNA-like region. The inflection point occurs very near the AUG start codon. Second, in the secondary structure model, nucleotides in the 5' regulatory domain were 1.7 times more likely to be paired than those in the 3' coding region. Although the 3' coding region was relatively unstructured overall, several structured regions with high pairing persistence punctuate the region. The most significant region spans positions 732-972. This element occurs at exactly the boundary between the matrix and capsid domains of the Gag polypeptide. Thus, it can be determined that RNA structure at this site modulates translation of the Gag polyprotein to facilitate independent folding of the matrix and capsid domains. Thus, hSHAPE is broadly useful for identifying novel regulatory motifs in cellular RNAs.

Structures for Distinct HIV Genome States

Comparison of the complete SHAPE reactivity profiles for the ex virio reference state with the other three states—in virio, AT-2 treated, and monomer—revealed that the distinct states contain extensive regions with identical structures. This was a remarkable result considering that the in virio RNA was maintained in its native conformation inside virions throughout the chemical modification step, whereas the monomer state was refolded in vitro after heating to 90° C. Thus, the functions of the HIV-1 genome are largely governed by a single predominant conformation.

In addition, analysis of the in virio state and comparison with the protein-free ex virio RNA revealed numerous regions that are persistently accessible to SHAPE chemistry. These regions are expected to hybridize readily with complementary sequences, including antisense and RNAi-based oligomers, and represent multiple new and attractive targets for anti-HIV therapeutics.

Reactivity profiles for these four states also showed structural differences, which can be interpreted in terms of important but local RNA conformation and protein-binding effects. There are three regions with significant differences between the ex virio reference state and the monomer RNA, which was refolded in vitro. The most dramatic difference was that the monomer RNA was much more reactive at positions 182 to 199. This region maps exactly to the tRNA(lys3) primer binding site and indicated that the primer remains paired to the HIV-1 RNA genome in viral particles. The ex virio state also had higher SHAPE reactivity at positions 161-166 and lower reactivity at positions 168-170, as compared with the monomer state. These reactivity changes were consistent with tRNA(lys3)-induced structural rearrangement at nucleotides 141-170 due to multi-site interactions between the tRNA and genomic RNA. The monomer state, which was not bound by tRNA, folds into a different local structure in these regions.

In all normal retroviral particles, the genomic RNA is in a dimeric form, with similar or identical RNA strands linked together by a limited number of base pairs and tertiary interactions. Dimerization is believed to involve an initial loop-loop interaction at the self-complementary sequence $G^{257}CGCGC^{262}$. These nucleotides were unreactive in both the monomer and ex virio states, which supports formation of constraining base pairing interactions at this loop. Thus, even the monomer state forms a loop-loop dimer. A similar early loop-loop dimer state has been identified for the Moloney murine sarcoma retrovirus (Badorrek et al. (2006) *PNAS USA* 103:13640-13645). No reactivity differences greater than 0.1 SHAPE units were observed between the monomer and ex virio RNAs in sequences flanking the 257-262 loop. This result was surprising because current models postulate that the stem sequences adjacent to this loop form a stable intermolecular duplex involving both genomic RNA strands. Similar SHAPE reactivities in this region do not support formation of an intermolecular duplex in mature HIV-1 viral particles, although a change yielding identical local nucleotide flexibilities in the pre- and post-dimer RNAs cannot be excluded.

Direct Analysis of NCp7-RNA Genome Interactions

NMIA is a small, mildly hydrophobic reagent that readily crosses the retroviral membrane. The structure of HIV-1 genomic RNA inside infectious virions was analyzed by treating viral particles with NMIA and then extracting and processing the modified RNA (the in virio state). Numerous reproducible differences between the ex virio and in virio states were observed that report virion-specific RNA structures and RNA-protein interactions.

The most prominent protein ligand for genomic RNA in mature HIV virions is the nucleocapsid protein. The nucleocapsid protein (NCp7) contains two highly conserved zinc-knuckle motifs comprised of cysteine and histidine residues that coordinate zinc ions and bind preferentially to guanosine. These compact motifs are flanked by positively charged residues that interact at adjacent RNA elements. Zinc ejecting agents such as 2,2'-dithioldipyridine (or AT-2) quantitatively disrupt interactions between the zinc ion and its cysteine ligands to compromise NCp7-RNA interactions, but leave the surface of the virus particle intact. Nucleocapsid-RNA interactions were disrupted in situ by treating virions with AT-2. The resulting genomic RNA was analyzed using hSHAPE.

Disrupting NCp7-RNA interactions by 'zinc-ejection' both increases and decreases local nucleotide flexibility in distinct genome regions. The effect of AT-2 treatment was highly specific because large regions of the genomic RNA in the intact in virio and AT-2 treated states show identical SHAPE reactivities. The strongest and most systematic effects of AT-2 treatment lie in the 5' regulatory domain and were largely absent after position 580 in the 3' coding region.

Regions showing a strong increase in SHAPE reactivity in the AT-2 treated state almost always resembled the protein-free ex virio state. A strong increase in reactivity in the AT-2 treated HIV RNA genomes at these sites reflected disruption of specific NCp7-RNA interactions. The single strongest NCp7 binding site was at positions 272-274, followed closely by positions 241-244. These sites, which had not been previously implicated in NCp7 or Gag recognition, were consistent with primary interaction motifs for the viral nucleocapsid domain at the 5' end of the HIV-1 genome.

Definition of a Nucleocapsid Interaction Domain

Inspection of the strongest NCp7 binding sites (positions 241-244, 272-274, 288-292, and 308-312), plus several secondary sites (positions 224-227, 318-320 and 326-329) indicated that the consensus NCp7 RNA recognition motif spans 1-2 guanosine residues in a single-stranded region of about 4 nucleotides adjacent to a helix. Most such sites were in a single domain in the model for the HIV-1 genome (positions 224-334). The domain overlaps structures that play a major role in HIV-1 genomic RNA packaging and also includes the $G^{257}CGCGC^{262}$ that forms intermolecular base pairs in the genomic RNA dimmer. Thus, it was concluded that the 223-334 domain dimer interacts, potentially cooperatively, with multiple copies of the HIV-1 NCp7 protein and with the nucleocapsid motif in the Gag protein. The specific juxtaposition of high affinity NCp7/Gag binding sites in the dimer functions as the structural motif that was specifically packaged in nascent HIV virions.

Structure Destabilizing Activity of the Nucleocapsid Domain hSHAPE analysis detected the non-specific binding of the nucleocapsid protein to nucleic acids to facilitate structural rearrangements. The presence of intact NCp7, prior to AT-2 treatment, increased SHAPE reactivity and flexibility in two regions of the genomic RNA. Local nucleotide flexibility was enhanced at five sites 5' of the tRNA primer binding site, which functioned to facilitate initial extension of the tRNA primer during the earliest stages of retroviral cDNA synthesis. Flexibility was also increased at nine sites 3' of the Gag start codon and might function to enhance either cDNA synthesis or translation by reducing RNA structure in this region.

HIV-1 RNA Transcripts

A DNA template encoding the 5' 976 nucleotides of the HIV-1 genome and containing a promoter for T7 RNA polymerase was generated by PCR (2 mL; 20 mM Tris-HCl (pH 8.4), 50 mM KCl, 2.5 mM $MgCl_2$, 0.5 µM forward (5'-TAATA CGACT CACTA TAGGT CTCTC TGGTT AGACC) (SEQ ID NO:1) and reverse (5'-CTATC CCATT CTGCA GCTTC C) (SEQ ID NO:2) primers, about 1 µg plasmid template containing a partial sequence of the HIV-1 pNL4-3 molecular clone (Genbank AF324493, obtained from the NIH AIDS Research and Reference Reagent Program), 200 µM each dNTP, and 25 units Taq polymerase; 34 cycles).

The PCR product was recovered by ethanol precipitation and resuspended in 300 µL TE buffer. Transcription reactions (3 mL; 37° C.; 5 hours; 40 mM Tris-HCl (pH 8.0), 5 mM $MgCl_2$, 10 mM DTT, 4 mM spermidine, 0.01% Triton X-100, 4% (w/v) PEG 8000, 300 µL PCR product, and 2 mM each NTP) were initiated by adding 0.1 mg/mL T7 RNA polymerase. The RNA product was precipitated and purified by denaturing polyacrylamide gel electrophoresis (5% acrylamide, 7 M urea), excised from the gel, and recovered by electroelution. The purified RNA (0.6 nmol) was resuspended in 100 µL TE buffer.

Modification of Transcript RNA

RNA (2 pmol) in 14.4 µL of ½× TE buffer was refolded by heating at 95° C., placing on ice, adding 3.6 µL folding buffer (250 mM Hepes-NaOH (pH 8), 1 M potassium acetate, pH 8, 25 mM $MgCl_2$), and incubating at 37° C. for 60 minutes. The folded RNA was divided equally between two tubes and treated with either NMIA (1 µL, 32 mM in DMSO) or neat DMSO (1 µL) and allowed to react for 60 minutes at 37° C. RNA from the (+) and (−) NMIA reagent experiments were recovered by ethanol precipitation and resuspended in 10 µL TE.

Detection of 2'-O-Adducts by Primer Extension

RNA (1 pmol, 10 µL, in 1×TE) corresponding to either the (+) or (−) NMIA reactions was heated to 95° C. for 3 minutes and cooled on ice for 1 minute. Fluorescently labeled primer (3 µL, complimentary to positions 342-363) was added to the (+) (0.2 µM Cy5) and (−) (0.4 µM WellRED D3) NMIA reactions, respectively, and primer-template solutions were incubated at 65° C. for 5 minutes and 35° C. for 10 minutes. Primer extension was initiated by the addition of enzyme mix (6 µL; 250 mM KCl; 167 mM Tris-HCl (pH 8.3); 1.67 mM each dATP, dCTP, dITP, dTTP; 10 mM $MgCl_2$; 52° C., 1 minute) and SUPERSCRIPT III™ reverse transcriptase (1 µL, 200 units). Extension continued at 52° C. for 15 minutes. Sequencing reactions used to identify peaks in the (+) and (−) reagents experiments were obtained using transcript RNA (1 pmol, in 9 µL TE), 3 µL primer (2 µM WellRED D2 or 1.2 µM LICOR IR 800), enzyme mix (6 µL), 1 µL of ddNTP solution (0.25 mM ddGTP or 10 mM other nucleotides), and SUPERSCRIPT III™ reverse transcriptase (1 µL). Depending on the quality of synthesis, primers were purified by denaturing gel electrophoresis (20% polyacrylamide, 1×TBE, 7 M urea; dimensions 0.75 cm×28.5 cm (w)×23 cm (h); 32 W; 90 minutes) and passively eluted into ½×TE overnight. The four reactions corresponding to a complete hSHAPE analysis ((+) NMIA, (−) NMIA, and two sequencing reactions) were combined, precipitated with ethanol in the presence of acetate, EDTA, and glycogen. Pellets were washed twice with 70% ethanol, dried under vacuum, and resuspended in deionized formamide. cDNA samples in 40 μL formamide were then separated on a 33 cm×75 μm capillary using a Beckman CEQ 2000XL DNA sequencer.

Example 4

Structures of the HIV-1 Genome Revealed by High-Throughput RNA Structure Analysis RNA Transcript Monomer A DNA template encoding the 5' 976 nucleotides of the HIV-1 genome and containing a promoter for T7 RNA polymerase was generated by PCR (2 mL; 20 mM Tris HCl (pH 8.4), 50 mM KCl, 2.5 mM $MgCl_2$, 0.5 μM forward (5'-TAATA CGACT CACTA TAGGT CTCTC TGGTT AGACC) (SEQ ID NO:1) and reverse (5'-CTATC CCATT CTGCA GCTTC C) (SEQ ID NO:2) primers, about 1 μg plasmid template containing a partial sequence of the HIV-1 pNL4-3 molecular clone (Genbank AF324493, obtained from the NIH AIDS Research and Reference Reagent Program), 200 μM each dNTP, and 25 units Taq polymerase; 34 cycles]. The PCR product was recovered by ethanol precipitation and resuspended in 300 μL TE (10 mM Tris, pH 8, 1 mM EDTA). Transcription reactions (3 mL; 37° C.; 5 h; 40 mM Tris (pH 8.0), 5 mM $MgCl_2$, 10 mM DTT, 4 mM spermidine, 0.01% Triton X-100, 4% (w/v) PEG 8000, 300 μL PCR product, and 2 mM each NTP) were initiated by adding 0.1 mg/mL T7 RNA polymerase. The RNA product was precipitated and purified by denaturing polyacrylamide gel electrophoresis (5% acrylamide, 7M urea), excised from the gel, and recovered by electroelution. The purified RNA (0.6 nmol) was resuspended in 100 μL TE.

Modification of Transcript RNA

RNA (2 pmol) in 14.4 μL of ½×TE was refolded by heating at 95° C., placing on ice, adding 3.6 μL folding buffer (250 mM Hepes (pH 8), 1 M potassium acetate, pH 8, 25 mM $MgCl_2$), and incubating at 37° C. for 60 minutes. The folded RNA was divided equally between two tubes and treated with either NMIA (1 μL, 32 mM in DMSO) or neat DMSO (1 μL) and allowed to react for 60 min at 37° C. RNA from the (+) and (−) NMIA reagent experiments was recovered by ethanol precipitation and resuspended in 10 μL TE.

HIV-1 Particle Production

VSV-G pseudotyped HIV-1 NL4-3 viral particles were produced by cotransfecting the pNL4-3 (Genbank AF324493) and pHCMV-G (VSV-G protein expression construct) plasmids at a ratio of 3:1 into 293T cells as described except that TransIT293 (Mirus Bio) was used to increase transfection efficiency. In sum, 40×150 $cm^2$ culture flasks, seeded at a density of 3×10⁶ 293T cells were transfected. Cultures were incubated for 48 hours and supernatants harvested, clarified by centrifugation at 5000 g for 10 min, filtered through a 0.2 μm membrane, and stored at 4° C. overnight. Cultures were incubated for an additional 24 hours with fresh culture media, and virus-containing supernatant was again collected using the same procedure. Supernatants from both harvests were pooled at 4° C. in preparation for treatment with the AT-2 and NMIA reagents. Viral particle genomes were quantified by real-time RT-PCR, the yield is typically 40 pmol HIV-1 RNA genomes/L cell culture.

HIV-1 Particle Treatment with AT-2

Aldrithiol-2 (AT-2, systematic name 2,2'-dithiodipyridine; 0.5 M in DMSO, 2.0 mL) or DMSO (2.0 mL) was added to 1.0 L virus supernatant and incubated overnight at 4° C. Virus particles from the (+) and (−) AT-2 experiments were pelleted separately by centrifugation (110,000 g, 4° C., 1.5 hours) through a 20% (w/v) sucrose cushion in phosphate buffered saline. Pellets were resuspended in 1.0 mL NMIA reaction buffer (50 mM Hepes (pH 8), 200 mM NaCl, 0.1 mM EDTA, and 10% fetal bovine serum).

NMIA Modification of Viral Particles

Concentrated samples of either purified viral particles or particles treated with AT-2 (500 μL) in NMIA reaction buffer were treated with NMIA (50 μL, 100 mM) or neat DMSO (50 μL) for 50 minutes at 37° C. The virus particle production, AT-2 treatment, and NMIA modification steps were performed as a single continuous process and without intermediate storage steps.

Extraction of HIV-1 Genomes from NMIA-Modified Particles

RNA genomes subjected to reaction with NMIA in virio were gently extracted from viral particles as described. In sum, concentrated samples of virus particles (in 550 μL NMIA buffer) were incubated at about 22° C. with 5 μL Proteinase K (20 mg/mL), 33.5 μL 1 M Tris-HCl (pH 7.5), 13.4 μL 5 M NaCl, 1.34 μL 0.5 M EDTA, 6.7 μL 1 M DTT, and 4 μL glycogen (20 mg/mL) for 30 minutes. RNA was purified by three consecutive extractions with phenol-chloroform, followed by precipitation with ethanol. Samples were resuspended in ½×TE to a concentration of 0.5 μM, based on quantitative RT-PCR analysis.

Extraction and SHAPE Analysis of HIV-1 Genomes from Native Particles

For the ex virio state, pelleted viral particles were dissolved in 1 mL of 50 mM Hepes (pH 8.0), 0.5 mM EDTA, 200 mM NaCl, 1% (w/v) SDS, and 100 μg/mL proteinase K and digested for 30 minutes at about 22° C. The RNA was then extracted against phenol-chloroform and the resulting deproteinized genomes were then aliquoted (2 pmol) and flash frozen at −80° C. For SHAPE analysis, the ex virio RNA was treated with NMIA using the same procedure as for modification of the monomer state (described above), except that the initial 90° C. heat step was omitted, and the time for incubation in folding buffer was reduced to 10 minutes.

Detection of 2'-O-Adducts by Primer Extension

In vitro transcript or authentic genomic RNA (1 pmol, 10 μL, in 1×TE) corresponding to either the (+) or (−) NMIA reactions was heated to 95° C. for 3 minutes and cooled on ice for 1 minute. Fluorescently labeled primer (3 μL) was added to the (+) (0.2 μM Cy5) and (−) (0.4 μM WellRED D3) NMIA reactions, respectively, and primer-template solutions were incubated at 65° C. for 5 minutes and 35° C. for 10 minutes.

Primer extension was initiated by addition of enzyme mix (6 μL; 250 mM KCl; 167 mM Tris-HCl (pH 8.3); 1.67 mM each dATP, dCTP, dITP, dTTP; 10 mM $MgCl_2$; 52° C., 1 minute) and SUPERSCRIPT III™ reverse transcriptase (1 μL, 200 units, Invitrogen). Extension continued at 52° C. for 15 minutes.

Sequencing reactions used to identify peaks in the (+) and (−) reagents experiments were obtained using transcript RNA (1 pmol, in 9 μL TE), 3 μL primer (2 μM WellRED D2 or 1.2 μM LICOR IR 800), enzyme mix (6 μL), 1 μL of ddNTP solution (0.25 mM ddGTP or 10 mM other nucleotides), and Superscript III (1 µL). Four sets of primers were used that were complementary to positions 342-363, 535-555, 743-762, or 956-976. Depending on the quality of synthesis, primers were purified by denaturing gel electrophoresis (20% polyacrylamide, 1×TBE, 7 M urea; dimensions 0.75 cm×28.5 cm (w)×23 cm (h); 32 W; 90 minutes) and passively eluted into ½×TE overnight.

The four reactions corresponding to a complete hSHAPE analysis ((+) NMIA, (−) NMIA, and two sequencing reactions) were combined, precipitated with ethanol in the presence of acetate, EDTA, and glycogen. Pellets were washed twice with 70% ethanol, dried under vacuum, and resuspended in deionized formamide. cDNA samples in 40 µL formamide were then separated on a 33 cm×75 µm capillary using a Beckman CEQ 200XL DNA sequencer.

Data Processing

Raw fluorescence intensity versus elution time profiles were analyzed using the signal processing framework in BaseFinder software modified as disclosed herein. Processing steps included (i) baseline correction, (ii) color separation to correct for spectral overlap of the fluorescent dyes such that each channel reported quantitative cDNA amounts, and (iii) mobility shift correction to align corresponding peaks in the four channels. Areas under each peak in the (+) and (−) NMIA traces were obtained by (i) peak detection and interpolation to align peaks in each channel with the RNA sequence and (ii) performing a whole trace Gaussian-fit integration. Integrated peak intensities were corrected for signal decay as a function of read length by assuming a constant probability for extension at each nucleotide position, after excluding the 2% of most highly reactive peaks:

$$D = Ap^{(elution\ time)} + C,$$

where D is the signal decay adjustment factor, A and C are scaling factors that reflect the arbitrary initial and final intensities of the trace, and p is the probability of extension at each nucleotide. Typical values for p spanned 0.995-0.999 for elution times in units of 2×sec. Each peak intensity calculated at the same elution time was divided by D. Individual data sets were normalized to a scale such that zero was the reactivity for unreactive positions and the average reactivity at flexible positions was set to 1.0. The normalization factor for each data set was determined by first excluding the most reactive 2% of peak intensities and then calculating the average for the next 8% of peak intensities. All reactivities were then divided by this average. Normalized hSHAPE reactivities from different primer extension reactions were then found to fall on the same absolute scale, without further adjustment. For each state, SHAPE information was obtained by combining information from four overlapping experiments, each repeated 2-3 times.

Incorporation of hSHAPE Constraints into RNAstructure.

SHAPE intensities were converted into a pseudo-energy term in the RNAstructure program using:

$$\Delta G_{SHAPE} = m\ \ln\ [SHAPE\ reactivity + 1.0] + b,$$

which was applied to each nucleotide in each stack of two base pairs. Therefore, the pseudo-energy was added twice per nucleotide paired in the interior of a helix and once per nucleotide paired at the end of a helix. The intercept, b, is the energy bonus for formation of a base pair with zero or low SHAPE reactivity while m, the slope, drives an increasing penalty for base pairing as the SHAPE reactivity increases. The b and m parameters were −0.6 and 1.7 kcal/mol, respectively (per nucleotide). The maximum allowed distance between base pairs was restrained to be 300 nucleotides or less. Increasing the maximum pairing distance to 600 nucleotides yielded a series of short, poorly predicted, and transient pairings that could be explained by shorter distance interactions. To determine the pairing persistence, structures were also computed for larger values of the b and m parameters, which has the effect of increasing the contribution of the SHAPE reactivity information on the secondary structure calculation. Helices considered to be highly predicted persisted even when these parameters were set to values as high as b=0 and m>4.

Summary of Examples

Using a concise set of experiments, single nucleotide resolution structural information for 94% of the first 900 nucleotides of the HIV-1 genomic RNA inside infectious virions have been obtained. Because SHAPE reactivities are quantitative and highly reproducible, structural differences between intact genomic RNA in authentic particles with three other instructive states could be interpreted, representing a total analysis of over 8,200 nucleotides. The comparisons support multiple new hypotheses for the intimate role of RNA genome structure in retroviral infectivity. Just as DNA sequencing has revolutionized our understanding of genome function, high-throughput RNA structure analysis will make possible analysis of the complete and intact RNAs that constitute a viral or cellular transcriptome, as a function of multiple biological states.

XI. OVERALL STEPS FOR SOFTWARE IMPLEMENTATION OF HIGH-THROUGHPUT RNA STRUCTURE ANALYSIS

Figure 7:
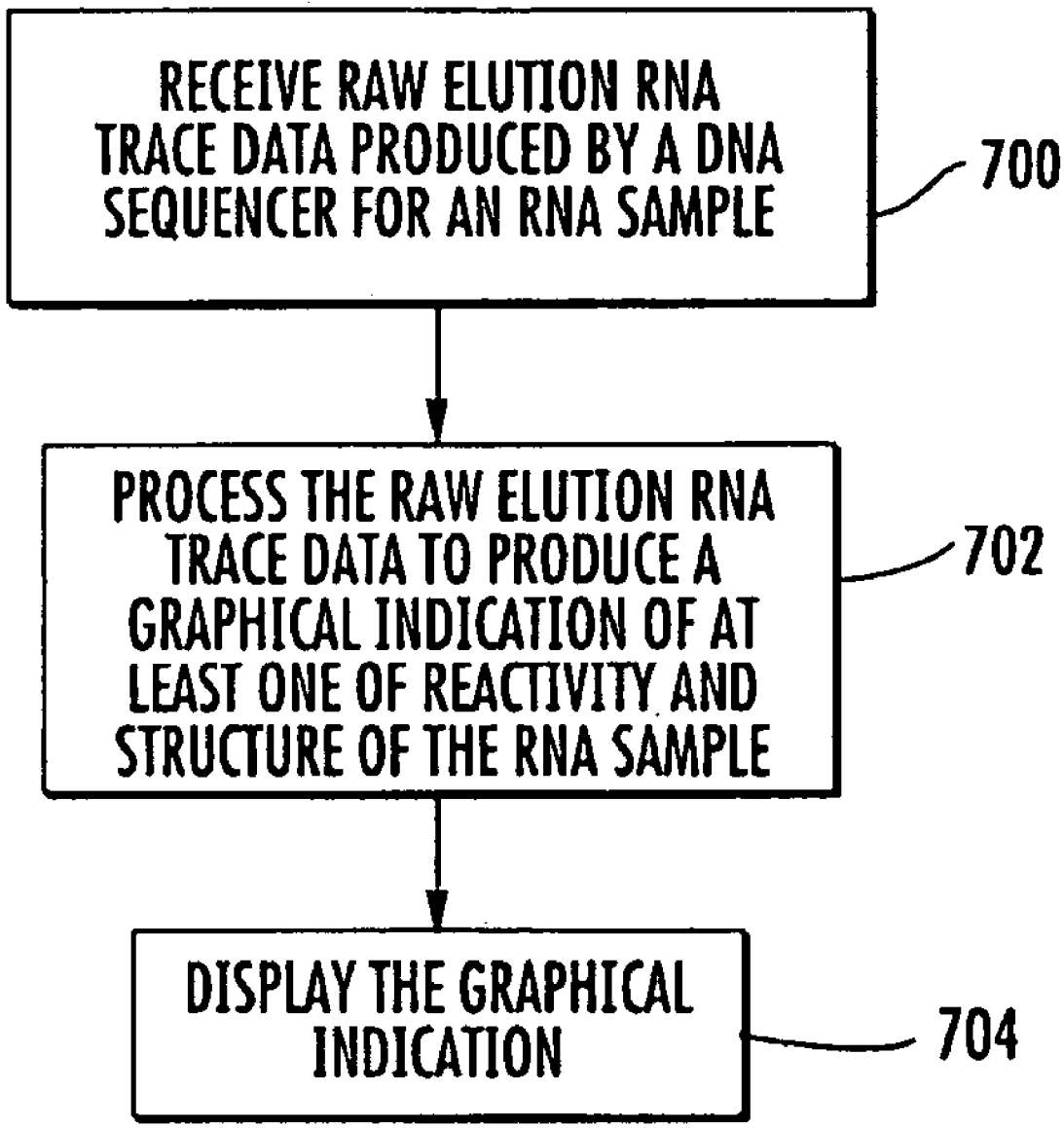
FIG. 7 is a flow chart illustrating exemplary overall steps for high-throughput RNA structure analysis using computer executable instructions according to an embodiment of the subject matter described herein.

As described in detail above, the subject matter described herein for high-throughput RNA structure analysis can be implemented in software. In general, the subject matter described herein for high-throughput RNA structure analysis can be implemented using a set of computer instructions, that when executed by a computer, performs a specific function. FIG. 7 is a flow chart illustrating the exemplary overall steps for high-throughput RNA structure analysis that can be implemented using computer executable instructions according to an embodiment of the subject matter described herein. Referring to FIG. 7, in step 700, raw elution RNA trace data produced by a DNA sequencer for an RNA sample is received. For example, as illustrated in FIG. 2, a DNA sequencer can produce a raw elution trace for an RNA sample and that raw trace data can be received by software, referred to herein as BaseFinder.

In step 702, the raw elution RNA trace data is processed to produce a graphical indication of at least one of the structure and the reactivity of the RNA sample. Referring again to FIG. 2, the BaseFinder program, when modified as described above, can apply the data processing described above to produce a graphical indication of the structure and/or reactivity of the RNA sample. An example of this graphical representation of reactivity as indicated appears in FIG. 3C where absolute SHAPE reactivities for positions in a sample are displayed. FIG. 3D illustrates an example of RNA structure superimposed with absolute band intensities.

Returning to FIG. 7, in step 704, the graphical indication is displayed to a user. For example, the graphical indication can be displayed to a user on a computer display device, such as a liquid crystal or a cathode ray tube display. Alternatively, the graphical indication can be displayed to the user by outputting the graphical indication to a printer and printing the graphical indication on paper or other suitable medium for viewing by the user.

REFERENCES

Badorrek et al. (2005) *Nature Chem Biol* 1:104-111.
Badorrek et al. (2006) *PNAS USA* 103:13640-13645.
Berkhout et al. (2002) *J Biol Chem* 277:19967-19975.
Chamberlin et al. (2000) *J Am Chem Soc* 122:216-224.
Chen et al. (2006) *EMBO J* 25:3156-3166.
Chetouani et al. (1997) *Nucleic Acids Res.* 25:3514-3522.
Coffin et al. (1997) *Retroviruses*, Cold Spring Harbor Press, Cold Spring Harbor, N.Y.
Damgaard et al. (2004) *J Mol Biol* 336:369-379.
Das et al. (2005) *RNA* 11:344-354.
Exner, O. (1978) Correlation Analysis in Chemistry; Plenum Press: New York).
Frankel et al. (1998) *Ann Rev Biochem* 67:1-25.
Fu et al. (1994) *J Virol* 68:5013-5018.
Giddinas et al. (1998) *Genome Res* 8:644-645.
Hogeweg et al. (1984) *Nucleic Acids Res.* 12:67-74.
Larson et al. (1987) *Mol. Cell. Biochem.* 74:5.
Mathews et al. (2004) *PNAS USA* 101:7287-7292.
Matzura et al. (1996) *CABIOS* 12:247-249.
Merino et al. (2005) *J Am Chem Soc* 127:4223-4231.
Nussinov et al. (1978) *J. Appl. Math.* 35:68-82.
Osterburg et al. (1981) *Comput. Progr. Biomed.* 13:101-109.
Paillart et al. (2002) *J Biol Chem* 277:5995-6004.
Paillart et al. (2004) *J Biol Chem* 279:48397-48403.
Thomas et al. (2006) *Virology* 353:41-51.
Tinoco et al. (1987) *Symp. Quant. Biol.* 52:135.
Tuerk et al. (1988) *PNAS USA* 85:1364.
Wilkinson et al. (2005) *J Am Chem Soc* 127:4659-4667.
Wilkinson et al. (2006) *Nature Protocols* 1:1610-1616.

It will be understood that various details of the presently claimed subject matter can be changed without departing from the scope of the presently claimed subject matter. Furthermore, the foregoing description is for the purpose of illustration only, and not for the purpose of limitation.

---

SEQUENCE LISTING

```
<160> NUMBER OF SEQ ID NOS: 10

<210> SEQ ID NO 1
<211> LENGTH: 35
<212> TYPE: DNA
<213> ORGANISM: Artificial Sequence
<220> FEATURE:
<223> OTHER INFORMATION: Artificially synthesized PCR primer employed in
      conjunction with SEQ ID NO: 2 to amplify a fragment of the HIV-1
      genome

<400> SEQUENCE: 1
taatacgact cactataggt ctctctggtt agacc                               35

<210> SEQ ID NO 2
<211> LENGTH: 21
<212> TYPE: DNA
<213> ORGANISM: Artificial Sequence
<220> FEATURE:
<223> OTHER INFORMATION: Artificially synthesized PCR primer employed in
      conjunction with SEQ ID NO: 1 to amplify a fragment of the HIV-1
      genome

<400> SEQUENCE: 2
ctatcccatt ctgcagcttc c                                             21

<210> SEQ ID NO 3
<211> LENGTH: 18
<212> TYPE: DNA
<213> ORGANISM: Artificial Sequence
<220> FEATURE:
<223> OTHER INFORMATION: Artificially synthesized primer extension
      primer

<400> SEQUENCE: 3
gaaccggacc gaagcccg                                                 18

<210> SEQ ID NO 4
<211> LENGTH: 14
<212> TYPE: DNA
<213> ORGANISM: Artificial Sequence
<220> FEATURE:
<223> OTHER INFORMATION: Artificially synthesized exemplary sequence
      determined during an hSHAPE experiment

<400> SEQUENCE: 4
ttgcccttca ccgc                                                     14
```

```
<210> SEQ ID NO 5
<211> LENGTH: 81
<212> TYPE: DNA
<213> ORGANISM: Artificial Sequence
<220> FEATURE:
<223> OTHER INFORMATION: Artificially synthesized sequence corresponding
      to yeast tRNAasp embedded in a structure cassette

<400> SEQUENCE: 5
caagccguga uagugggcgc uugucgcgug ccagaucggg guucaauucc ccgucgcggc    60
gccaucgauc cgguucgccg g                                             81

<210> SEQ ID NO 6
<211> LENGTH: 14
<212> TYPE: DNA
<213> ORGANISM: Artificial Sequence
<220> FEATURE:
<223> OTHER INFORMATION: Artificially synthesized sequence employed as a
      5' flanking sequence in a structure cassette

<400> SEQUENCE: 6
aaccgggcuu ccgg                                                     14

<210> SEQ ID NO 7
<211> LENGTH: 43
<212> TYPE: DNA
<213> ORGANISM: Artificial Sequence
<220> FEATURE:
<223> OTHER INFORMATION: Artificially synthesized sequence employed as a
      3' flanking sequence in a structure cassette

<400> SEQUENCE: 7
ucgauccggu ucgccggauc caaaucgggc uucggguccgg uuc                    43

<210> SEQ ID NO 8
<211> LENGTH: 104
<212> TYPE: DNA
<213> ORGANISM: Artificial Sequence
<220> FEATURE:
<223> OTHER INFORMATION: Artificially synthesized sequence corresponding
      to the TAR and Poly(A) stem loops of the HIV-1 genome

<400> SEQUENCE: 8
ggucucucug guuagaccag aucugagccu gggagcucuc uggcuaacua gggaacccac    60
ugcuuaagcc ucaauaaagc uugccuugag ugcucaaagu agug                   104

<210> SEQ ID NO 9
<211> LENGTH: 13
<212> TYPE: DNA
<213> ORGANISM: Artificial Sequence
<220> FEATURE:
<223> OTHER INFORMATION: Artificially synthesized sequence corresponding
      to a portion of the HIV-1 genome

<400> SEQUENCE: 9
uaugggcaag cag                                                      13

<210> SEQ ID NO 10
<211> LENGTH: 154
<212> TYPE: DNA
<213> ORGANISM: Artificial Sequence
<220> FEATURE:
<223> OTHER INFORMATION: Artificially synthesized sequence corresponding
      to the specificity domain of Bacillus subtilis RNase P
```

```
<400> SEQUENCE: 10
ucgugccuag cgaagucaua agcuagggca gucuuuagag gcugacggca ggaaaaaagc      60
cuacgucuuc ggauauggcu gaguauccuu gaaagugcca cagugacgaa gucucacuag     120
aaauggugag aguggaacgc gguaaacccc ucga                                 154
```

What is claimed is:

1. A method of forming a covalent ribose 2'-O-adduct within an RNA molecule, the method comprising contacting an electrophile with RNA wherein the electrophile selectively modifies unconstrained nucleotides in the RNA to form a covalent ribose 2'-O-adduct, wherein the electrophile is the isatoic anhydride derivative 1-methyl-7-nitroisatoic anhydride (1M7).

2. A method of forming a covalent ribose 2'-O-adduct within an RNA molecule, the method comprising contacting an electrophile with RNA wherein the electrophile selectively modifies unconstrained nucleotides in the RNA to form a covalent ribose 2'-O-adduct, wherein the electrophile is the phthalic anhydride derivative 4 nitrophthalic anhydride (4NPA).

3. The method of claim 1 or claim 2, wherein the RNA is present in a biological solution.

4. A covalent ribose 2'-O-adduct within an RNA molecule formed by the method of claim 1.

5. A covalent ribose 2'-O-adduct, comprising RNA and an electrophile bound at the 2'-O position of one or more unconstrained nucleotides in the RNA, wherein the electrophile is selected from the group consisting of 1M7 and 4NPA.

* * * * *